(12) United States Patent
Jones et al.

(10) Patent No.: US 9,714,290 B2
(45) Date of Patent: Jul. 25, 2017

(54) HUMANISED ANTI CTLA-4 ANTIBODIES

(75) Inventors: Timothy David Jones, Babraham (GB); Robert George Edward Holgate, Royston (GB); Francis Joseph Carr, Balmedie (GB)

(73) Assignee: ANTITOPE LIMITED, Cambridge (GB)

( * ) Notice: Subject to any disclaimer, the term of this patent is extended or adjusted under 35 U.S.C. 154(b) by 268 days.

(21) Appl. No.: 14/003,900

(22) PCT Filed: Mar. 9, 2012

(86) PCT No.: PCT/EP2012/054144
§ 371 (c)(1),
(2), (4) Date: Dec. 18, 2013

(87) PCT Pub. No.: WO2012/120125
PCT Pub. Date: Sep. 13, 2012

(65) Prior Publication Data
US 2014/0105914 A1    Apr. 17, 2014

Related U.S. Application Data

(60) Provisional application No. 61/450,896, filed on Mar. 9, 2011.

(30) Foreign Application Priority Data

Mar. 9, 2011    (GB) .................................. 1103955.9

(51) Int. Cl.
| | | |
|---|---|---|
| C07K 16/28 | (2006.01) |
| A61K 39/395 | (2006.01) |
| A61K 45/06 | (2006.01) |
| G01N 33/68 | (2006.01) |
| A61K 39/00 | (2006.01) |

(52) U.S. Cl.
CPC ...... *C07K 16/2818* (2013.01); *A61K 39/0011* (2013.01); *A61K 39/39558* (2013.01); *A61K 45/06* (2013.01); *G01N 33/6893* (2013.01); *A61K 2039/505* (2013.01); *C07K 2317/24* (2013.01); *C07K 2317/55* (2013.01); *C07K 2317/56* (2013.01); *C07K 2317/622* (2013.01); *C07K 2317/76* (2013.01)

(58) Field of Classification Search
None
See application file for complete search history.

(56) References Cited

U.S. PATENT DOCUMENTS

2002/0198143 A1    12/2002    Ruben et al.

FOREIGN PATENT DOCUMENTS

| | | |
|---|---|---|
| JP | 2003-512819 | 4/2003 |
| JP | 2003-520828 | 7/2003 |
| JP | 2005-087215 | 4/2005 |
| JP | 2007-534304 | 11/2007 |
| JP | 2009-213478 | 9/2009 |
| JP | 2010-505929 | 2/2010 |
| WO | 00/37504 | 6/2000 |
| WO | 01/14424 | 3/2001 |
| WO | 01/018021 | 3/2001 |
| WO | 01/54731 | 8/2001 |
| WO | 03/086459 | 10/2003 |
| WO | 2005/042581 | 5/2005 |
| WO | 2006/082406 | 8/2006 |
| WO | 2008/044032 | 4/2008 |

OTHER PUBLICATIONS

International Search Report for PCT/EP2012/054144, all pages, mailed Apr. 24, 2012.

*Primary Examiner* — Ilia Ouspenski
(74) *Attorney, Agent, or Firm* — Nixon & Vanderhye PC

(57) ABSTRACT

The invention provides an anti-CTLA4 antibody which inhibits the binding of CTLA4 to human B7, in particular, it inhibits binding of CTLA4 to human B7.1 and/or human B7.2. Specific antibodies are provided with specific variable region sequences as well as compositions comprising such antibodies for use in treating disease.

19 Claims, 17 Drawing Sheets

FIG. 9A

Figure 1:
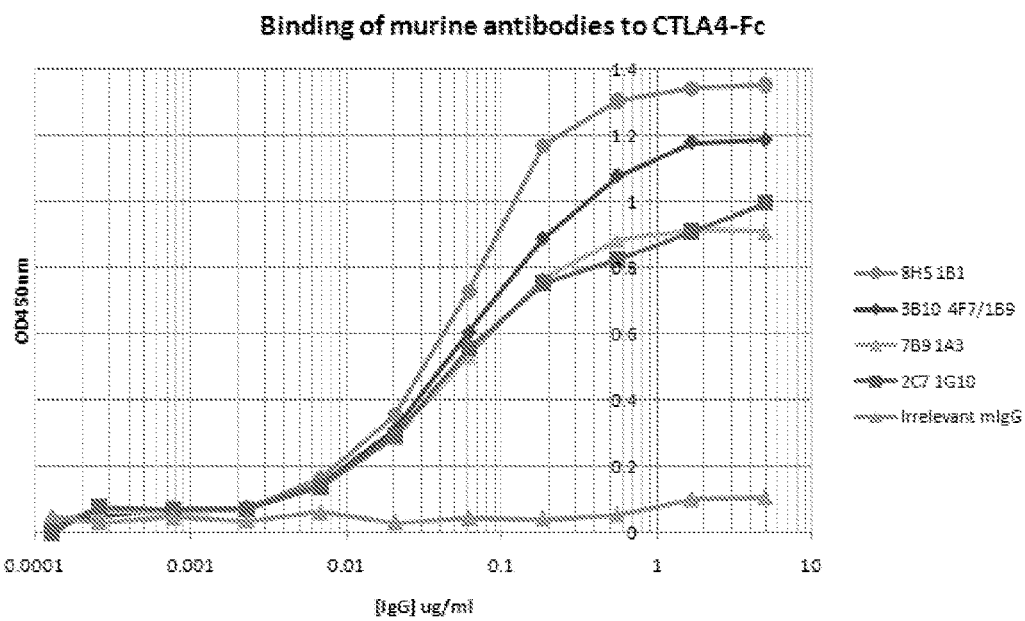

3B10 Hybridoma VH DNA (SEQ ID No. 1)

```
GAGGTCCAGC TGCAACAGTT TGGAGCTGAA CTGGTGAAGC CTGGGGCTTC    50
AGTGAAGATG TCCTGCAAGG CTTCTGGCTA CACATTCACT GACTACAACA   100
TGGACTGGGT GAGGCAGAGC CATGGAAAGA GTCTTGAGTG GATCGGAAAT   150
ATTAATCCTA ACTCTGAGAG TACTAGTTAC AACCAGAAGT TCAAGGGAAA   200
GGCCACATTG ACTGTAGACA AGTCCTCCAG CACAGCCTAC ATGGAGCTCC   250
GCAGCCTGAC ATCTGATGAC ACTGCAGTCT ATTACTGTAC AAGAGACGGG   300
AATAGGTACG ACGCCTGGTT TGCTTACTGG GGCCAAGGGA CTCTGGTCAC   350
TGTCTCCTCA                                               360
```

FIG. 9B

3B10 Hybridoma VK DNA (SEQ ID No. 2)

```
CAGATTGTTC TCACCCAGTC TCCAGCAATC ATGTCTGCAT CTCCAGGGGA    50
GAAGGTCACC ATGACCTGCA GTGCCAGCTC AAGTGTTACT TACATGCACT   100
GGTTCCAGCA GAAGCCAGGC ACTTCTCCCA AACTCTGGAT TTATAGCACA   150
TCCATCCTGG CTTCTGGAGT CCCTGCTCGC TTCAGTGGCA GTGGATCTGG   200
GACCTCTTAC TCTCTCACAA TCAGCCGAAT GGAGGCTGAA GATGCTGCCA   250
CTTATTACTG CCAGCAAAGG ACTAGTTACC CGCTCACGTT CGGTACTGGG   300
ACCAAGCTGG AGCTGAAA                                      318
```

FIG. 10A

8H5 Hybridoma VH DNA (SEQ ID No. 5)

```
CAGGTCCAGC TGCAACAGTC TGGAGATGAT CTGGTAAAGC CTGGGGCCTC    50
AGTGAAGCTG TCCTGCAAGG CTTCTGGCTA CACCTTCACC AGCTACTGGA   100
TTAACTGGAT AAAACAGAGG CCTGGACAGG GCCTTGAGTG GATAGGACGT   150
ATTGCTCCTG GAAGTGGTAC TACTTACTAC AATGAAGTGT TCAAGGGCAA   200
GGCAACACTG ACTGTAGACA AATATTCCAG CACAGCCTAC ATTCAGCTCA   250
GCAGCCTGTC ATCTGAGGAC TCTGCTGTCT ATTTCTGTGC AAGAGGGGAC   300
TATGGTTCTT ACTGGGGCCA AGGGACTCTG GTCACTGTCT CCTCA        345
```

FIG. 10B

8H5 Hybridoma VK DNA (SEQ ID No. 6)

```
CAAATTGTTC TCACCCAGTC TCCAGCAATC ATGTCTGCAT CTCCAGGGGA    50
GAAGGTCACC ATGACCTGCA GTGCCAGCTC AAGTATAAGT TACATGCACT   100
GGTTCCAGCA GAAGCCAGGC ACCTCCCCCA AAAGATGGAT TTATGACACA   150
TCCAAACTGG CTTCTGGAGT CCCTGCTCGC TTCAGTGGCA GTGGGTCTGG   200
GACCTCTTAT TCTCTCACAA TCAACAGCAT GGAGGCTGAA GATGCTGCCA   250
CTTATTACTG CCATCAGCGG ACTAGTTACC CACTCACGTT CGGTGCTGGG   300
ACCAAGCTGG AGCTGAAA                                      318
```

FIG. 11A

3B10 Hybridoma VH Amino Acid (SEQ ID No. 3)

FIG. 11B

3B10 Hybridoma VK Amino Acid (SEQ ID No. 4)

FIG. 12A

8H5 Hybridoma VH Amino Acid (SEQ ID No. 7)

FIG. 12B

8H5 Hybridoma VK Amino Acid (SEQ ID No. 8)

FIG. 13

Humanised 3B10 variant VH amino acid sequences (SEQ ID Nos. 3 and 31 to 35)

Humanised 3B10 variant VK amino acid sequences (SEQ ID Nos. 4 and 36 to 40)

Humanised 8H5 variant VH amino acid sequences (SEQ ID Nos. 7 and 41 to 45)

Humanised 8H5 variant VK amino acid sequences (SEQ ID Nos. 8 and 46-50)

Human Mixed Lymphocyte Reaction Model

Tumour Animal Model

FIG. 20

| Sequence | Name-Pool |
|---|---|
| ATGRASTTSKGGYTMARCTKGRTTT | MuIgV$_H$5'-A |
| ATGRAATGSASCTGGGTYWTYCTCTT | MuIgV$_H$5'-B |
| ATGGACTCCAGGCTCAATTTAGTTTTCCT | MuIgV$_H$5'-C |
| ATGGCTGTCYTRGBGCTGYTCYTCTG | MuIgV$_H$5'-C |
| ATGGVTTGGSTGTGGAMCTTGCYATTCCT | MuIgV$_H$5'-C |
| ATGAAATGCAGCTGGRTYATSTTCTT | MuIgV$_H$5'-D |
| ATGGRCAGRCTTACWTYYTCATTCCT | MuIgV$_H$5'-D |
| ATGATGGTGTTAAGTCTTCTGTACCT | MuIgV$_H$5'-D |
| ATGGGATGGAGCTRTATCATSYTCTT | MuIgV$_H$5'-E |
| ATGAAGWTGTGGBTRAACTGGRT | MuIgV$_H$5'-E |
| ATGGRATGGASCKKIRTCTTTMTCT | MuIgV$_H$5'-E |
| ATGAACTTYGGGYTSAGMTTGRTTT | MuIgV$_H$5'-F |
| ATGTACTTGGGACTGAGCTGTGTAT | MuIgV$_H$5'-F |
| ATGAGAGTGCTGATTCTTTTGTG | MuIgV$_H$5'-F |
| ATGGATTTTGGGCTGATTTTTTTTATTG | MuIgV$_H$5'-F |
| CCAGGGRCCARKGGATARACIGRTGG | MuIgGV$_H$3'-2 |
| ATGRAGWCACAKWCYCAGGTCTTT | MuIgkV$_L$5'-A |
| ATGGAGACAGACACACTCCTGCTAT | MuIgkV$_L$5'-B |
| ATGGAGWCAGACACACTSCTGYTATGGGT | MuIgkV$_L$5'-C |
| ATGAGGRCCCCTGCTCAGWTTYTTGGIWTCTT | MuIgkV$_L$5'-D |
| ATGGGCWTCAAGATGRAGTCACAKWYYCWGG | MuIgkV$_L$5'-D |
| ATGAGTGTGCYCACTCAGGTCCTGGSGTT | MuIgkV$_L$5'-E |
| ATGTGGGGAYCGKTTTYAMMCTTTTCAATTG | MuIgkV$_L$5'-E |
| ATGGAAGCCCCAGCTCAGCTTCTCTTCC | MuIgkV$_L$5'-E |
| ATGAGIMMKTCIMTTTCAITTCYTGGG | MuIgkV$_L$5'-F |
| ATGAKGTHCYCIGCTCAGYTYCTIRG | MuIgkV$_L$5'-F |
| ATGGTRTCCWCASCTCAGTTCCTTG | MuIgkV$_L$5'-F |
| ATGTATATATGTTTGTTGTCTATTTCT | MuIgkV$_L$5'-F |
| ATGAAGTTGCCTGTTAGGCTGTTGGTGCT | MuIgkV$_L$5'-G |
| ATGGATTTWCARGTGCAGATTWTCAGCTT | MuIgkV$_L$5'-G |
| ATGGTYCTYATVTCCTTGCTGTTCTGG | MuIgkV$_L$5'-G |
| ATGGTYCTYATVTTRCTGCTGCTATGG | MuIgkV$_L$5'-G |
| ACTGGATGGTGGGAAGATGGA | MuIgkV$_L$3'-1 |

FIG. 21

| Sequence | Name |
|---|---|
| ctgttgctacgcgtgtccactccGAGGTCCAGCTGCAACAG | 3B10 VH 5' |
| ctgccccagaaagcttaccTGAGGAGACAGTGACCAGAG | 3B10 VH 3' |
| ggctcccaggcgcgcgatgtCAGATTGTTCTCACCCAGTC | 3B10 VK 5' |
| tagaattgcgggatccaactgaggaagcaaagtttaaattctactcacgTTTCAGCTCCAGCTTGGTC | 3B10 VK 3' |
| ctgttgctacgcgtgtccactccCAGGTCCAGCTGCAACAG | 8H5 VH 5' |
| ctgccccagaaagcttaccTGAGGAGACAGTGACCAGAG | 8H5 VH 3' |
| ggctcccaggcgcgcgatgtCAAATTGTTCTCACCCAGTCTC | 8H5 VK 5' |
| tagaattgcgggatccaactgaggaagcaaagtttaaattctactcacgTTTCAGCTCCAGCTTGGTCC | 8H5 VK 3' |

HUMANISED ANTI CTLA-4 ANTIBODIES

This application is the U.S. national phase under 35 U.S.C. 371 of International Application No. PCT/EP2012/054144 filed 9 Mar. 2012, which designated the U.S. and claims priority to GB 1103955.9, filed 9 Mar. 2011, and U.S. Provisional Application No. 61/450,896, filed 9 Mar. 2011; the entire contents of each of which are hereby incorporated by reference.

The present invention relates to the treatment and prevention of human diseases using novel humanised antibodies against human CTLA4 and methods of treating or preventing human diseases using these antibodies.

BACKGROUND TO THE INVENTION

The vertebrate immune system requires multiple molecular and cellular interactions to achieve optimal immune responses. In particular, activation of T lymphocytes (T cells) is an important component of many such responses. Antigen-presenting cells (APC) can activate T cells by presentation of antigens via peptides carried by major histocompatibility complex (MHC) molecules to the TCR (T cell receptor). Such activation also requires co-stimulation by APC. Delivery of a non-specific costimulatory signal to T cell requires at least two homologous B7 family members found on APC, B7-1 (also called B7, B7.1, or CD80) and B7-2 (also called B7.2 or CD86), both of which can deliver costimulatory signals on binding to the CD28 antigen on T cells resulting in T cell activation. CD28 is a homodimeric glycoprotein member of the immunoglobulin (Ig) superfamily with a single extracellular variable region, and is present on most mature human T cells.

A homologue of CD28 named CTLA4 (Cytotoxic Lymphocyte Associated Antigen, also designated CD152) was discovered in 1987 (Brunet et al., (1987) Nature 328:267-270) with particular association with cytotoxic T cells. As with CD28, CTLA4 is a member of the Ig superfamily and comprises a single extracellular Ig domain. However, the role of CTLA4 is primarily to inhibit T cell activation and this was shown in CTLA4 deficient mice (Chambers et al., (1997) Immunity. 7:8855-8959) which suffer from massive lymphoproliferation. In addition, blockage of CTLA4 was shown to enhance T cell responses in vitro (Walunas et al., (1994)) Immunity. 1:405-413 and in vivo (Kearney (1995) J. Immunol. 155:1032-1036) and also to increase antitumour immunity (Leach (1996) Science. 271:1734-1736). Therefore, blockage of CTLA4 might provide new treatments for disease, especially human diseases where immune stimulation might be beneficial such as for treatment of cancers and infectious diseases.

Development of blockers of CTLA4 function has focused on the use of monoclonal antibodies, especially antibodies derived from transgenic mice engrafted with genes encoding human immunoglobulins (and deficient in host mouse immunoglobulin genes). Clinical trials are ongoing with such antibodies including Ipilimumab (Keler et al., J Immunol 171:6251-6259 (2003)), which is an IgG1 isotype, and Tremelimumab (Ribas et al., Oncologist 12: 873-883 (2005)) which is an IgG2 isotype. Whilst the immunogenicity (induction of antibodies against the injected human monoclonal antibodies) is generally reported to be low, there is concern that such human antibodies, due to somatic mutations and rearrangements in the variable region sequences (which may result in T cell epitopes), may induce immunogenicity in some patients resulting in adverse effects and lack of therapeutic effect. There is thus a need for improved anti-CTLA4 monoclonal antibodies with a potentially lower immunogenicity in order to provide more effective treatments of human diseases.

SUMMARY OF THE INVENTION

The present invention relates to novel humanised antibodies which specifically bind to human CTLA4. The invention also provides humanised antibodies where binding to human CTLA4 inhibits the binding of human CTLA4 to human B7. The invention also provides humanised antibodies that bind to human CTLA4 with an equilibrium dissociation constant (Kd) of at least $10^{-8}$M. The invention also provides humanised antibodies that specifically bind to human CTLA4 that block binding of human CTLA4 to human B7 by at least about 10%, 20%, 30%, 40%, 50%, 60%, 70%, 80%, 90%, 99%, or 100%. The invention also provides humanised antibodies that specifically bind to human CTLA4 having an antibody heavy chain of either isotype IgG1, IgG2, IgG3 or IgG4, or having a mutated IgG constant region, for example to inhibit binding to Fc receptors or to inhibit binding to complement. The invention also provides humanised antibodies wherein the antibody light chain is a kappa light chain. The humanised antibody can be encoded by human IgG heavy chain and human kappa light chain nucleic acids that encode protein sequences in their variable regions as set forth in SEQ ID NO:31 through SEQ ID NO:50. In a preferred embodiment of the present invention, the humanised antibody comprises variable regions from SEQ ID NO:45 and SEQ ID NO:49 (otherwise referred to as "VH5:VK4').

The present invention also provides humanised antibodies that specifically bind to human CTLA4 whereby the antibody variable regions have been selected or modified to exclude one or more human CD4+ T cell epitopes. The present invention also provides human antibodies that specifically bind to human CTLA4 whereby the antibody variable regions have been formed primarily by fusing segments of sequences from existing human antibody variable region sequences.

The present invention also provides humanised antibodies of the invention comprising heavy chain CDR1, CDR2, and CDR3 amino acid sequences, "DYNMD" (SEQ ID No. 9), "NINPNSESTSYNQKFKG" (SEQ ID No. 10) and "DGNRYDAWFAY" (SEQ ID No. 11), respectively, and light chain CDR1, CDR2, and CDR3 amino acid sequences, "SASSSVTYMH" (SEQ ID No. 12), "STSILAS" (SEQ ID No. 13), and "QQRTSYPLT" (SEQ ID No. 14), respectively.

The present invention also provides humanised antibodies of the invention comprising heavy chain CDR1, CDR2, and CDR3 amino acid sequences, "SYWIN" (SEQ ID No. 15), "RIAPGSGTTYYNEVFKG" (SEQ ID No. 16) and "GDYGSY" (SEQ ID No. 17), respectively, and light chain CDR1, CDR2, and CDR3 amino acid sequences, "SASSSISYMH" (SEQ ID No. 18), "DTSKLAS" (SEQ ID No. 19), and "HQRTSYPLT" (SEQ ID No. 20), respectively.

Humanised antibodies of the present invention can be composed of any of the above CDR sequences SEQ ID No. 9 to SEQ ID No. 20 and minor variants of these CDR sequences where alterations of one or more amino acids does not significantly alter binding to human CTLA4. Humanised antibodies can be created by joining together the CDR sequences with sequences from human variable region frameworks where such framework sequences are derived from single or multiple other human antibody variable region framework sequences. Commonly such human variable region framework sequences will include one or more mutations which contribute to optimal or improved binding of the humanised antibodies to CTLA4. In a preferred embodiment of the present invention, such human variable region framework sequences in the humanised antibodies are derived entirely from sequences in other human antibody variable regions as described in methods of EP1844074 (Antitope Ltd). These sequences comprise joined segments of sequences from other human antibody variable regions, together with human constant regions. In particular, such humanised antibodies also contain CDR sequences derived from CDR sequences, framework sequences or part framework/CDR sequences from other human antibody variable regions together with human constant regions, thus creating humanised antibodies in which the variable region sequences are derived entirely from sequences in other human antibody variable regions together with human constant regions, thus creating a "fully human" antibody.

The invention also provides humanised antibodies that specifically bind to human CTLA4, wherein said humanised antibody is produced by a mammalian cell line, especially CHO or NS0 cells. The invention also provides a humanised antibody that specifically binds to human CTLA4 that is a Fab fragment or a single chain Fv (scFv). The invention also provides multispecific antibodies (two or more different antibody molecules joined together to give two or more different specifities) including at least one humanised antibody from the sequences SEQ ID NOS:31 to 35 for the heavy chain and SEQ ID NOS:36 to 40 for the light chain for antibody 3B10; or humanised antibody from the sequences SEQ ID NOS:41 to 45 for the heavy chain and SEQ ID NOS:46 to 50 for the light chain for the antibody 8H5, each of which specifically binds to human CTLA4. In a preferred embodiment, the invention provides multispecific antibodies with variable regions consisting of SEQ ID NOS:45 for the heavy chain and SEQ ID NOS:49 for the light chain. The different antibodies included in each multispecific antibody can be linked to each other either covalently or non-covalently.

The invention provides a pharmaceutical composition comprising a humanised antibody that specifically binds to human CTLA4 and a pharmaceutically acceptable carrier. The pharmaceutical composition can further comprise an agent effective to induce an immune response against a target antigen, or one or more chemotherapeutic agents.

The invention provides a method for inducing, augmenting or prolonging an immune response to an antigen in a patient, comprising administering to the patient an effective dosage of a humanised antibody that specifically binds to human CTLA4, wherein the antibody blocks binding of human CTLA4 to human B7. The antigen can include a tumour antigen, an antigen associated with a pathogen, an antigen associated with a disease of the central nervous system (CNS), an antigen associated with diseases of the blood system including hypertension and atherosclerosis, an antigen associated with an inflammatory disease including rheumatoid arthritis and autoimmune diseases, or an antigen associated with an allergy. Tumour antigens can be one or more antigens on the cell surface of a tumour, one or more molecules which interact with the tumour, one or more MHC complexes of peptides derived from tumour antigens, or antigens not directly associated with tumours but where immune responses to the antigen will have an adverse effect on the tumour such as antigens associated with the tumour vasculature. Pathogens can be a virus, a bacterium, a fungus or a parasite. CNS antigens include beta amyloid associated with plaque deposits in Alzheimer's disease. Blood system antigens include integrins and adhesins, as well as antigens associated with plaque deposits in atherosclerosis. Inflammatory disease antigens include cytokines and cytokine receptors. Allergy antigens include antigens associated with food, plant, chemical and environmental allergens. The method of the invention can also include administering the antigen, or a fragment or an analogue thereof, to the patient, whereby the antigen in combination with the humanised antibody induces, augments or prolongs the immune response.

The invention also provides a method of suppressing an immune response in a patient, comprising administering to the patient an effective dosage of a multivalent preparation comprising at least two humanised antibodies to human CTLA4 linked to each other resulting, for example, in the induction of regulatory T cells or the down regulation of CTLA4. The invention also provides a method of suppressing an immune response in a patient, comprising administering to the patient an effective dosage of a polyclonal preparation comprising at least two humanised antibodies to human CTLA4.

The present invention further provides humanised monoclonal antibodies which specifically bind to human CTLA4, as well as compositions containing one or a combination of such antibodies. Some of the humanised antibodies of the invention are characterised by binding to human CTLA4 with high affinity, and/or by blocking the interaction of human CTLA4 with its ligand, the human B7-1 and B7-2 molecules. Accordingly, such humanised antibodies of the invention can be used as diagnostic or therapeutic agents in vivo and in vitro.

The humanised antibodies of the invention can encompass various antibody isotypes, or mixtures thereof, such as IgG1, IgG2, IgG3, IgG4, IgM, IgA1, IgA2, IgAsec, IgD, IgE or mutated forms of these IgGs such as mutations which reduce of eliminate binding to Fc receptors. Typically, they include IgG4 (e.g. IgG4k) and IgG1 (e.g. IgG1k). The humanised antibodies can be full-length (e.g., an IgG4 or IgG1 antibody) or can include only an antigen-binding portion (e.g., a Fab, F(ab')2, Fv or a scFv fragment).

Some humanised anti-CTLA4 antibodies of the present invention can be characterised by one or more of the following properties: a) specificity for human CTLA4 (specifically binding to human CTLA4); b) a binding affinity to human CTLA4 with an equilibrium dissociation constant (Kd) of at least $10^{-8}$M.

In another aspect, the invention provides nucleic acid molecules encoding the humanised antibodies, or antigen-binding portions, of the invention. Accordingly, recombinant expression vectors that include the antibody-encoding nucleic acids of the invention, and host cells transfected with such vectors, are also encompassed by the invention, as are methods of making the antibodies of the invention by culturing these host cells.

Anti-human CTLA4 humanised monoclonal antibodies of the invention, or antigen binding portions thereof (e.g., Fab), can be derivatised or linked to another functional molecule, e.g., another peptide or protein (e.g., a Fab' fragment). For example, an antibody or antigen-binding portion of the humanised antibodies of the invention can be functionally linked (e.g., by chemical coupling, genetic fusion, noncovalent association or otherwise) to one or more other molecular entities. For example, the humanised anti-CTLA4 antibody, or antigen binding fragment thereof, can be conjugated to a therapeutic moiety, e.g., a cytotoxic drug, an enzymatically active toxin, or a fragment thereof, a radioisotope, a therapeutic nucleic acid, or a small molecule anti-cancer drug. The antibodies of the invention can also be conjugated to cytotoxic pharmaceuticals, e.g., radiolabeled with a cytotoxic agents such as, e.g. 131I, or can be coupled to a ribosome inactivating protein, e.g. *pseudomonas* exotoxin (PE38 fragment, plant or bacterial toxins such as ricin, the α-chain of ricin, saporin, pokeweed antiviral protein, diphtheria toxin, or *Pseudomonas* exotoxin A (Kreitman and Pastan (1998) *Adv. Drug Delivery Rev.* 31:53.).

In another aspect, the present invention provides compositions, e.g., pharmaceutical and diagnostic compositions, comprising a pharmaceutically acceptable carrier and at least one humanised monoclonal antibody of the invention, or an antigen-binding portion thereof, which specifically binds to human CTLA4. Some compositions may also comprise a combination of the humanised antibodies or antigen-binding portions of the invention. Such compositions may also comprise combinations with one or more other biologically active molecules as separate molecules, for example, a combination of at least one humanised monoclonal antibody of the invention and another biologically active molecule, or may combine combinations with one or more other biologically active molecules in the same molecule, for example as a bispecific or multispecific molecule either as a combination of two or more humanised antibodies of the invention or as a combination with one or more other biologically active molecules.

For in vivo methods, the antibody, or antigen-binding portion thereof (or a bispecific or multispecific molecule of the invention), can be administered to a human subject suffering from a T-cell-related disease, or a disease that can be ameliorated or prevented by inducing, augmenting, prolonging or suppressing an immune response.

Humanised monoclonal antibody compositions of the invention also can be administered in combination with other known therapies, e.g., an anti-cancer therapy. Accordingly, the invention provides a method for treating cancer in a subject comprising administering a therapeutically effective amount of a pharmaceutical composition of a humanised antibody together with a pharmaceutical carrier to the subject. Some such methods include combination with a vaccine. Some such vaccines include a tumour cell vaccine, a GM-CSF-modified tumour cell vaccine, a nucleic acid (such as DNA) vaccine, and a tumour-associated antigen or an antigen-loaded dendritic cell vaccine.

Humanised antibodies to human CTLA4 can be used in methods of treatment requiring either stimulation of immune responses or suppression. Stimulation is achieved using antibodies that block binding of human CTLA4 to human B7 and diseases amenable to treatment by stimulation and augmentation of prolonging of immune responses include cancers of the prostate, kidney, colon, lung or breast; pathogenic infections; diseases associated with the CNS e.g. amyloidogenic diseases including Alzheimer's disease; and diseases with inflammatory or allergic components. Immunosuppression can also be achieved using humanised antibodies to human CTLA4, for example through induction of regulatory T cells (Coquerelle et al., *Gut* 2009; 58:1363-1373). Diseases amenable to treatment include graft versus host disease, host versus graft disease, allergy, autoimmune diseases and other inflammatory diseases.

In yet another aspect, the present invention provides a method using antibodies of the invention for detecting in vitro or in vivo the presence of human CTLA4 antigen in a sample, e.g., for diagnosing a human CTLA4-related disease. In some methods, this is achieved by contacting a sample to be tested, along with a control sample, with a humanised monoclonal antibody of the invention, or an antigen-binding portion thereof (or a bispecific or multispecific molecule), under conditions that allow for formation of a complex between the antibody and human CTLA4. Complex formation is then detected (e.g., by ELISA) in the test samples, and any statistically significant increase in the formation of complexes between the test and control samples is indicative the presence of human CTLA4 antigen in the test sample.

It will be understood by those skilled in the art that the humanised antibodies of the present invention will have additional uses or compositions beyond those described herein, in all cases where the humanised antibody binds to human CTLA4 antigen whereby such uses and compositions shall be considered to be within the scope of the invention. It will be understood by those skilled in the art that the variable region sequences of the humanised antibodies of the present invention (SEQ ID NO:31 through SEQ ID NO:50) or CDRs of the humanised antibodies of the present invention (SEQ ID NO:9 through SEQ ID NO:20) may be subject to variations which do not significantly change the properties of the humanised antibodies of the present invention whereby such variants shall be considered to be within the scope of the invention. In addition, such variations either within the variable region or CDR sequences of the humanised antibodies should be considered to be within the scope of the present invention where the variable region sequences of such variants have significant homology to the humanised sequences of the present invention. For example, a variant nucleic acid may be determined to be within the scope of the invention where this includes sequences containing or substantially identical to SEQ ID NO:21 through SEQ ID NO:30 as determined by its ability to hybridise under stringent conditions to a nucleic acid of the present invention. In one embodiment, a nucleic acid sequence can be determined to be within the scope of the invention (e.g., is substantially identical to SEQ ID NO:21 through SEQ ID NO:30) by its ability to hybridise under stringent conditions to a nucleic acid within the scope of the invention (such as SEQ ID NO:21 through SEQ ID NO:30). The term "hybridise" refers to the binding, duplexing, or hybridising of a molecule to a particular nucleotide sequence under stringent hybridisation conditions when that sequence is present in a complex mixture (e.g. total cellular or library DNA or RNA), wherein the particular nucleotide sequence is detected at least at about 10 times background. Stringent hybridisation conditions will be selected, for example, to be 5-10° C. lower than the thermal melting point (Tm) for the specific sequence at a defined ionic strength pH.

EXAMPLES

The following examples shall not be considered as limiting to the scope of the invention. The figures and tables relate to the examples below and are as follows;

FIG. 1—binding of murine antibodies to CTLA4-Fc.

Figure 2:
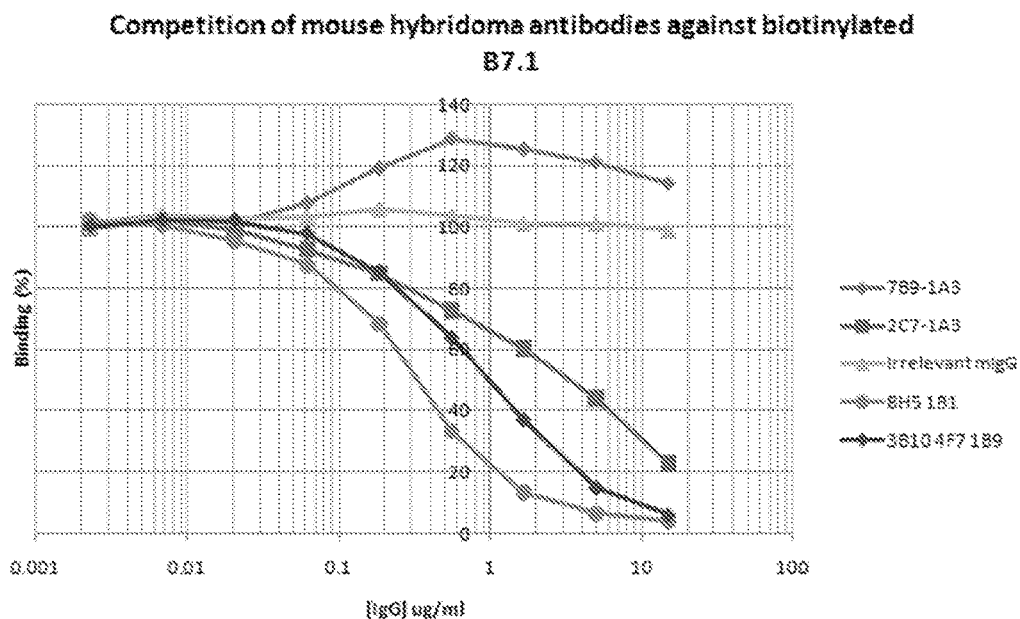

FIG. 2—competition ELISA of murine antibodies for binding to CTLA4-Fc against biotinylated B7.1.

Figure 3:
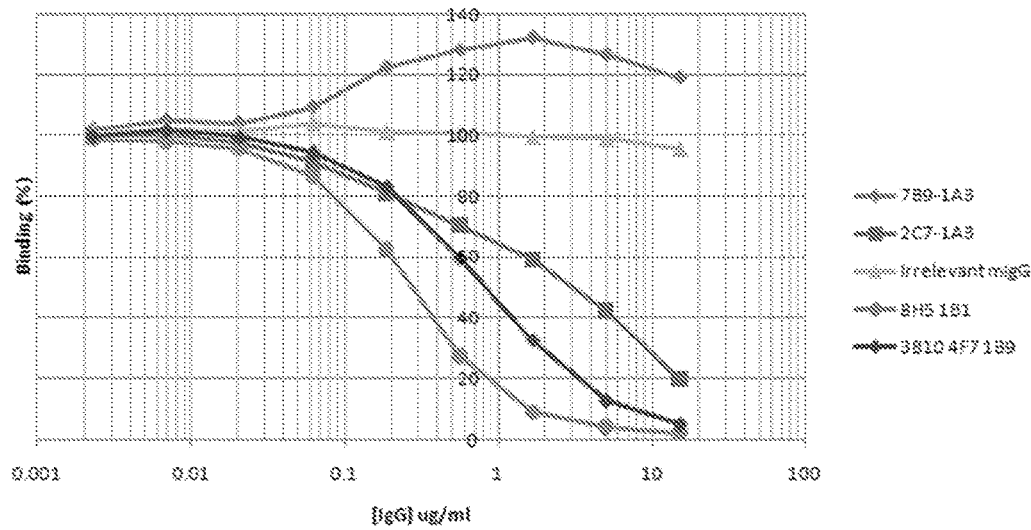

FIG. 3—competition ELISA of murine antibodies for binding to CTLA4-Fc against biotinylated B7.2.

Figure 4:
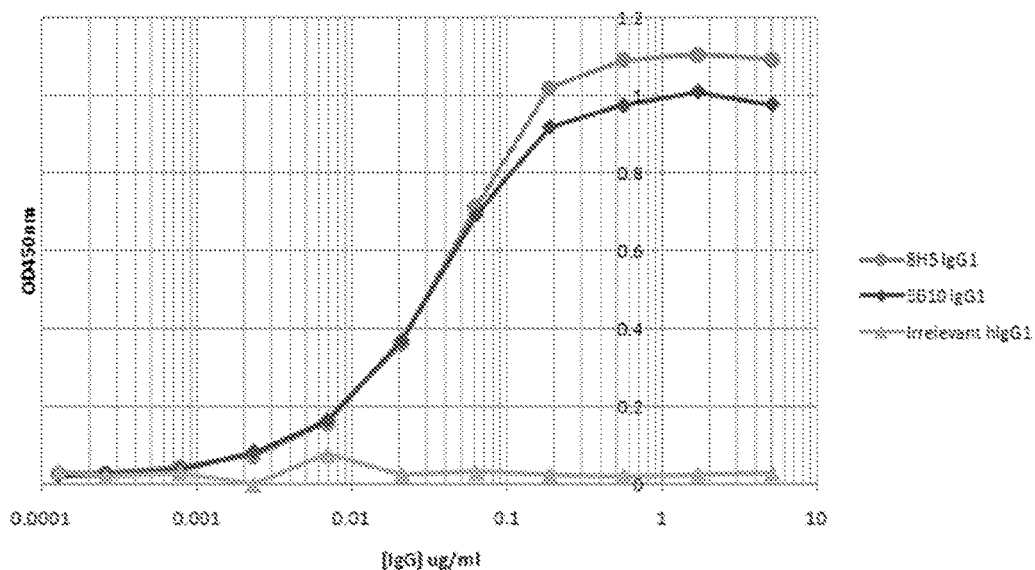

FIG. 4—binding of chimeric 3B10 and 8H5 human IgG1 antibodies to CTLA4-Fc.

Figure 5:
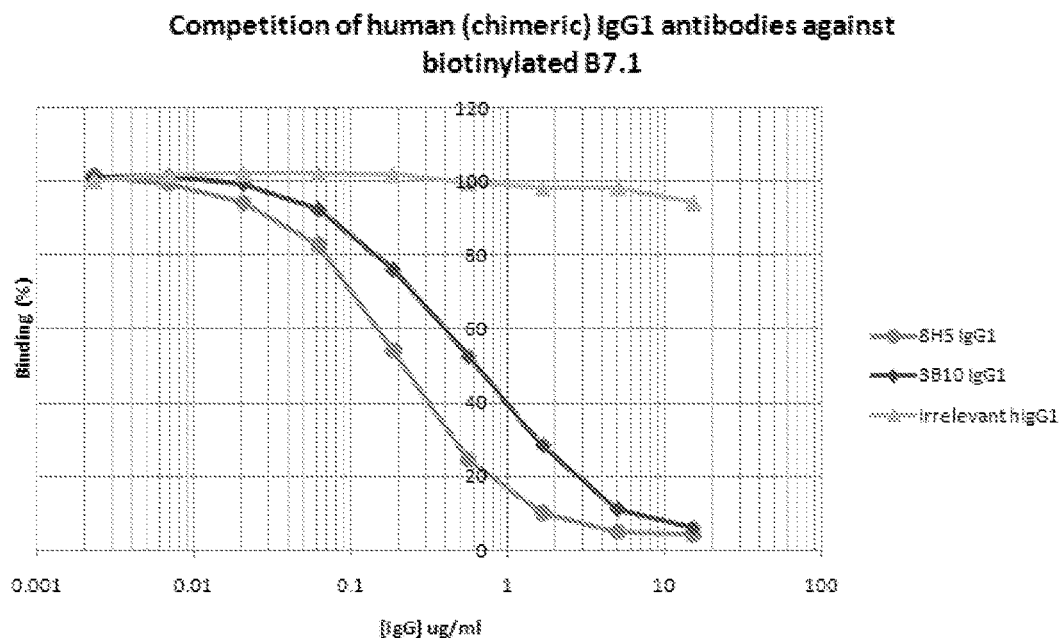

FIG. 5—competition ELISA of chimeric 3B10 and 8H5 human IgG1 antibodies for binding to CTLA4-Fc against biotinylated B7.1.

Figure 6:
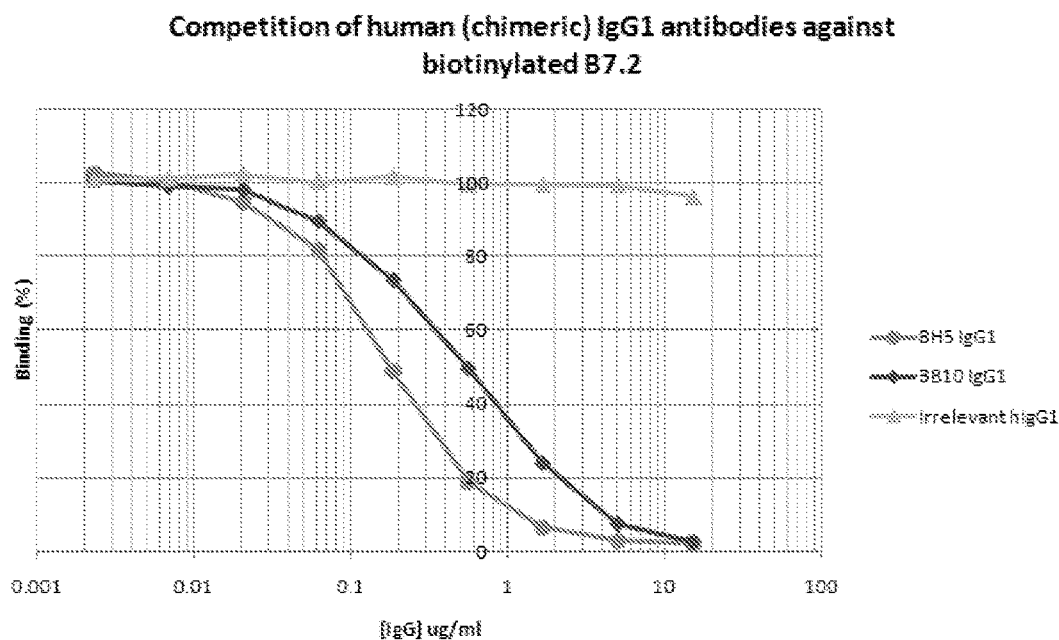

FIG. 6—competition ELISA of chimeric 3B10 and 8H5 human IgG1 antibodies for binding to CTLA4-Fc against biotinylated B7.2.

Figure 7A:
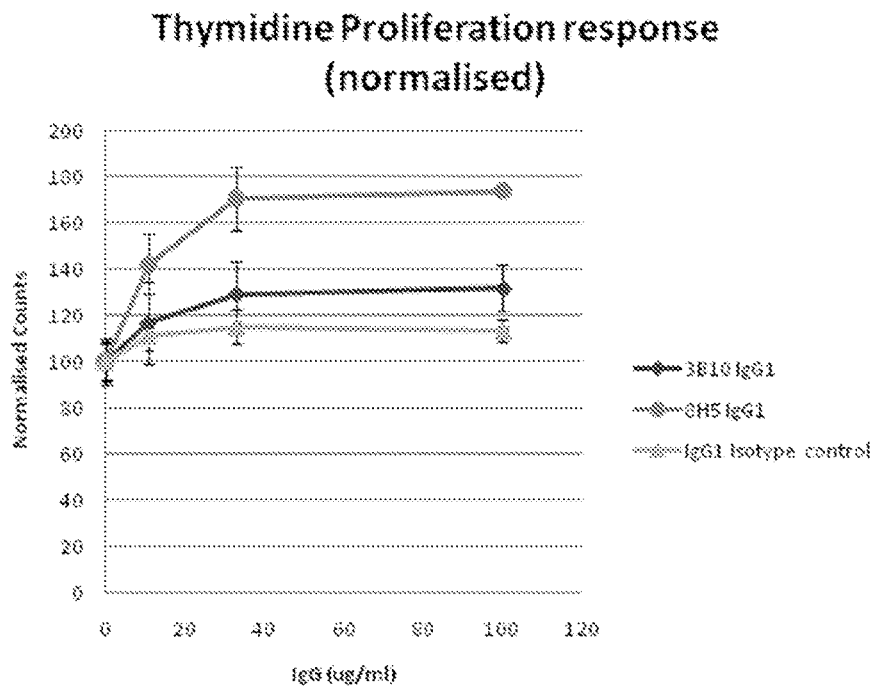

FIGS. 7A (first study) and 7B (second study)—T cell proliferation of human PBMC in response to chimeric 3B10 and 8H5 human IgG1 antibodies.

Figure 8A:
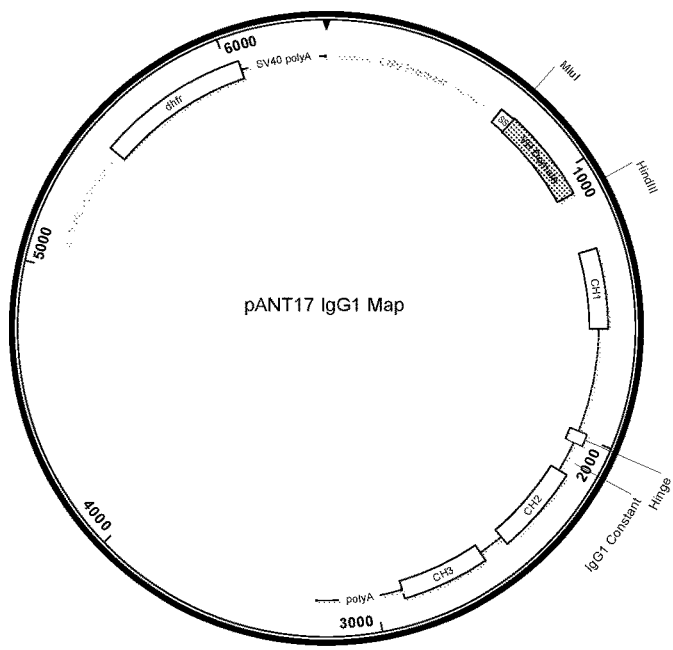
Figure 8B:
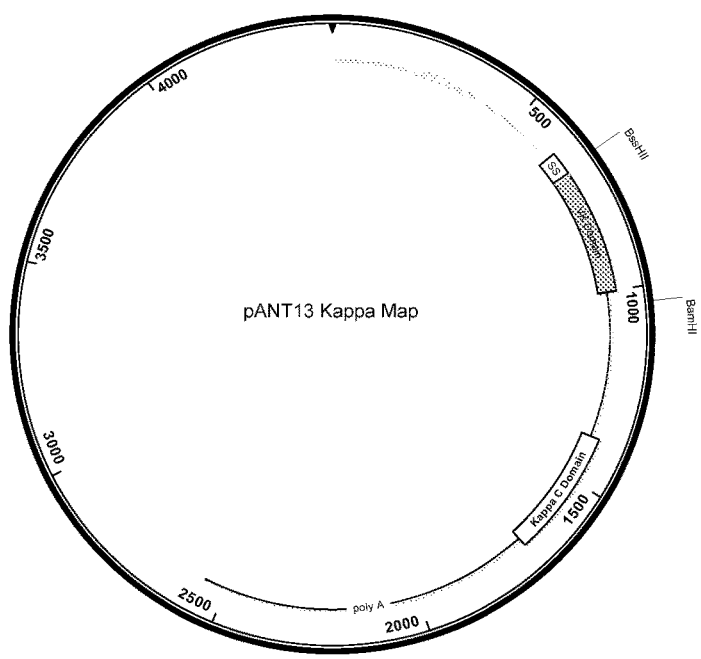

FIGS. 8A and 8B—pANT17 IgG1 (FIG. 8A) and pANT13 Kappa (FIG. 8B) antibody expression vector maps.

FIGS. 9A and 9B—3B10 variable region (VH FIG. 9A and VK FIG. 9B) DNA sequences.

FIGS. 10A and 10B—8H5 variable region (VH FIG. 10A and VK FIG. 10B) DNA sequences.

Figures 11A, 11B:
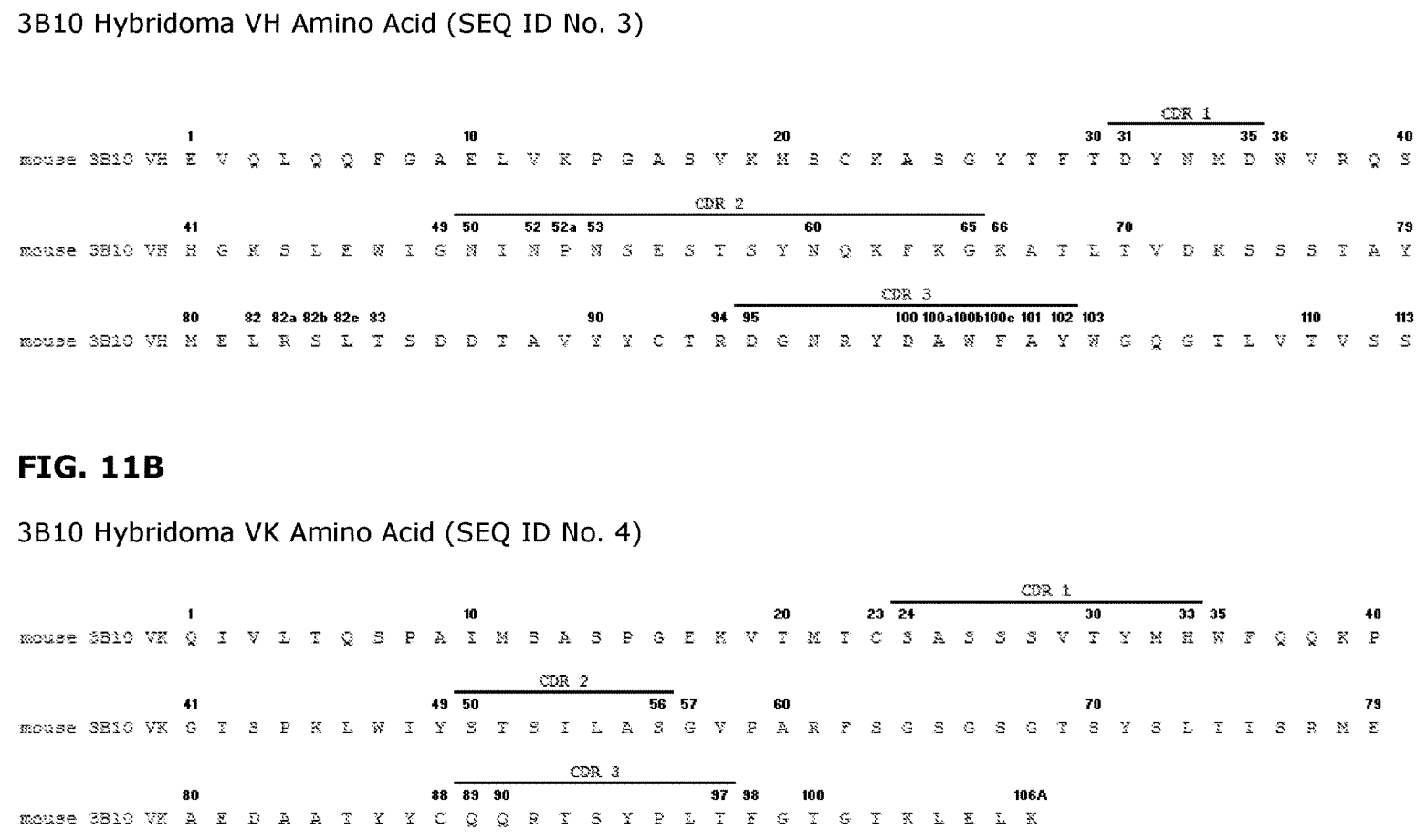

FIGS. 11A and 11B—3B10 VH (FIG. 11A) and VK (FIG. 11A) amino acid sequences.

Figures 12A, 12B:
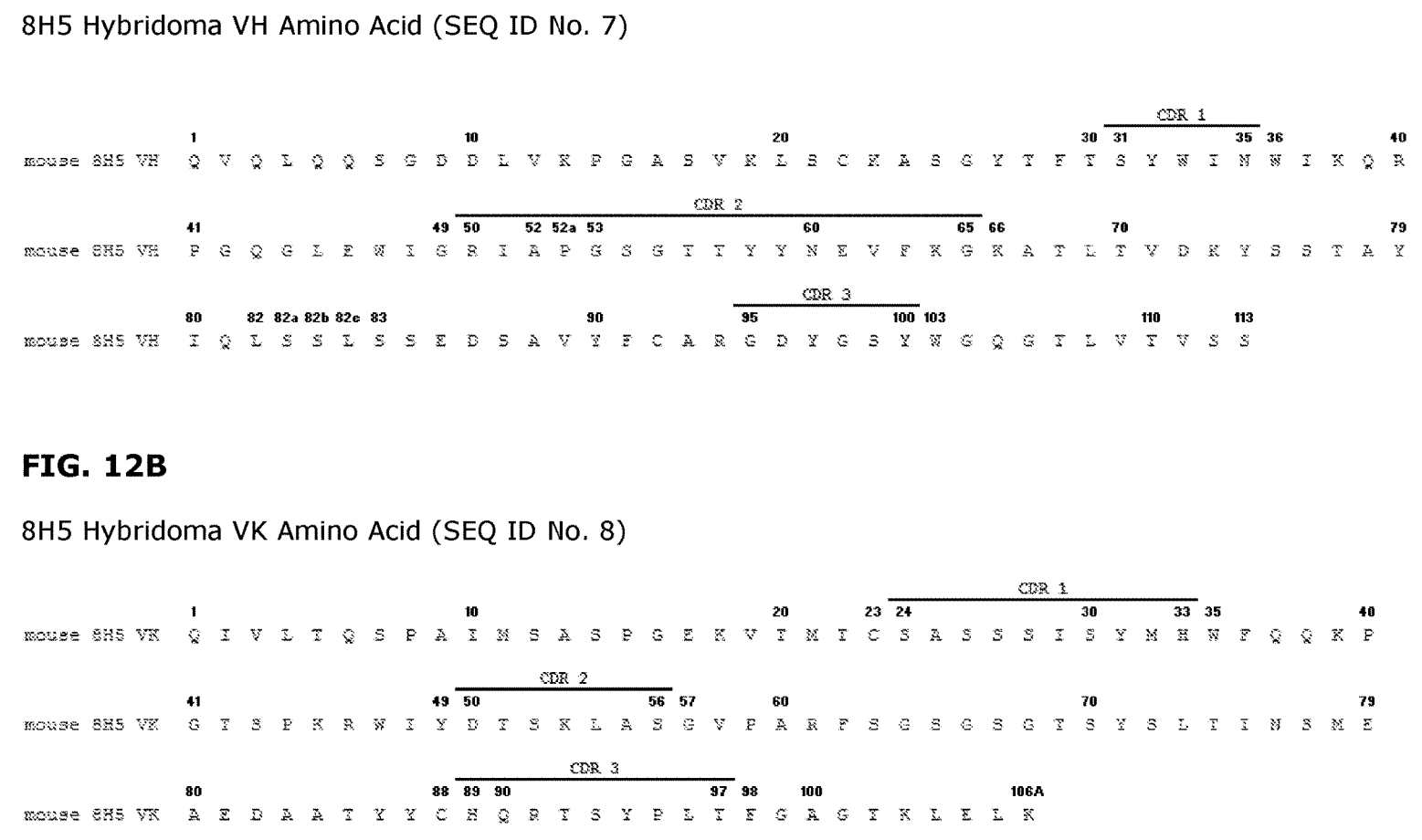

FIGS. 12A and 12B—8H5 VH (FIG. 12A) and VK (FIG. 12B) amino acid sequences.

Figure 13:
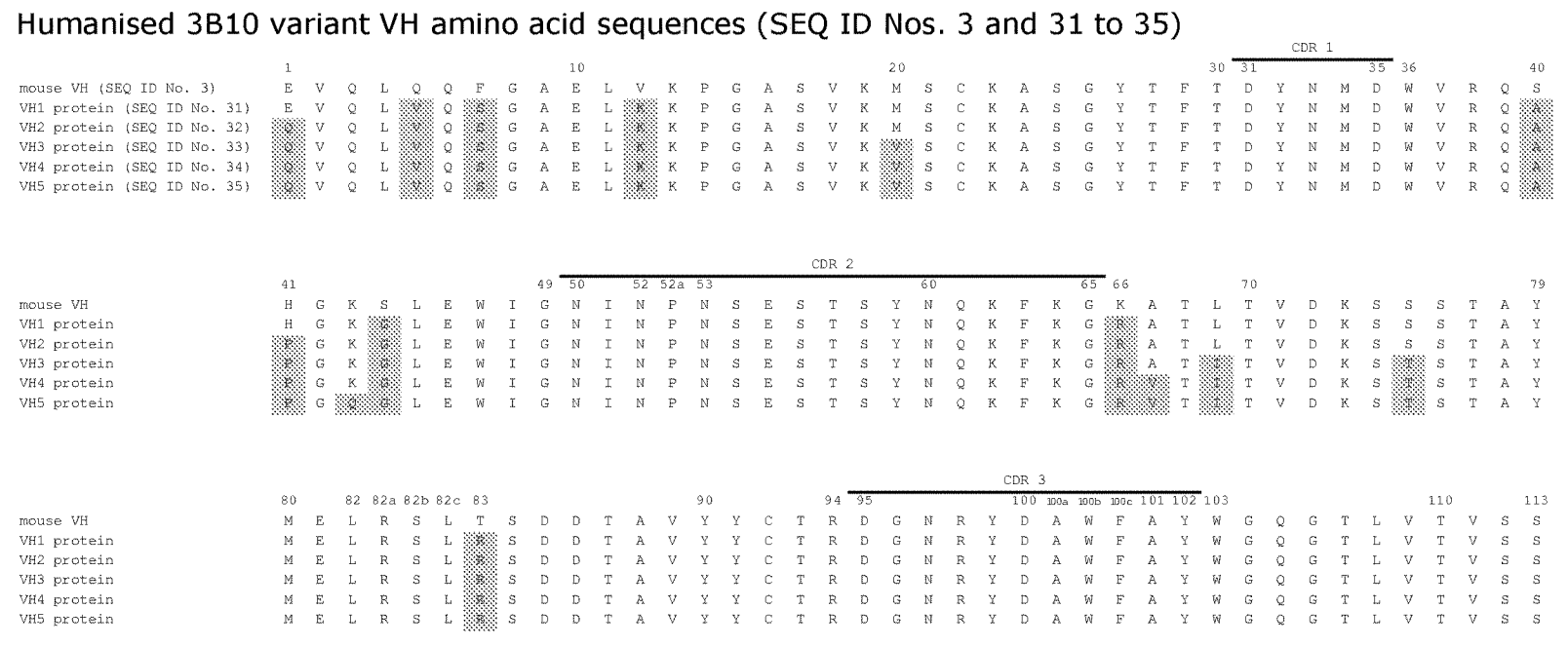

FIG. 13—Humanised 3B10 VH amino acid sequences.

Figure 14:
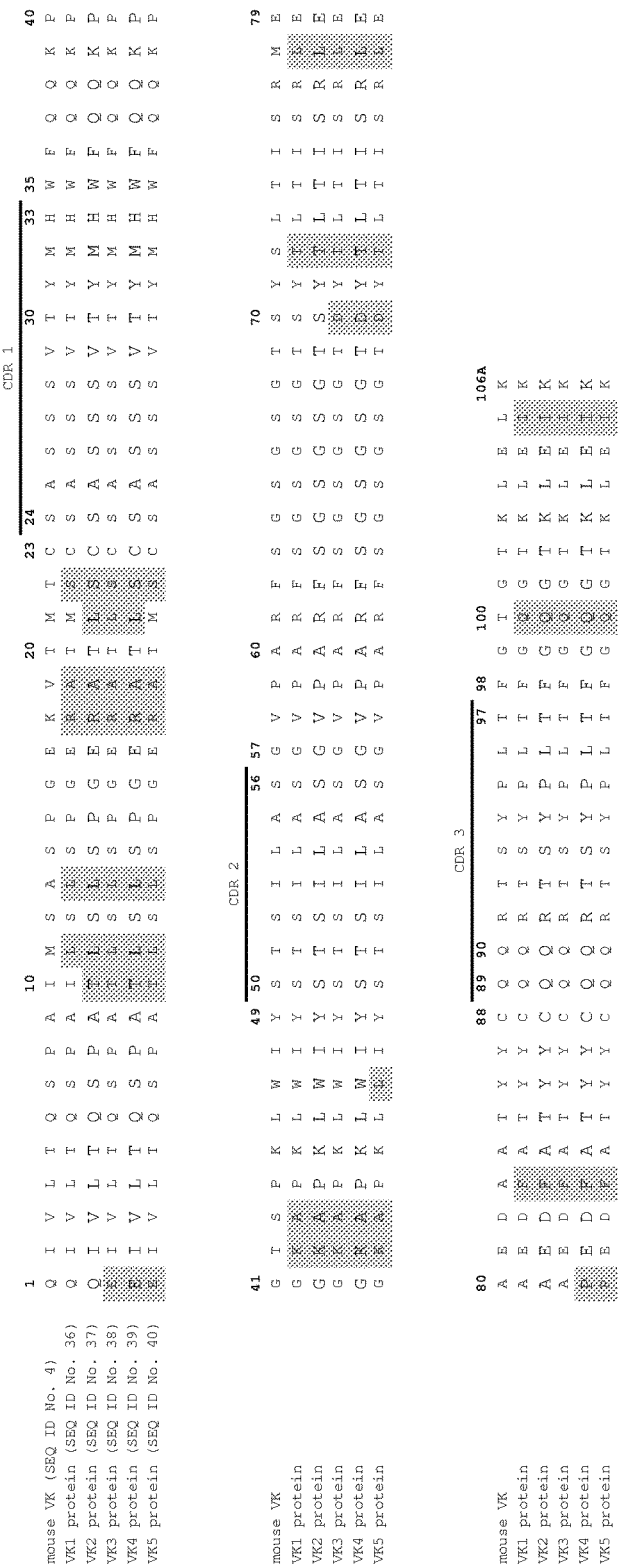

FIG. 14—Humanised 3B10 VK amino acid sequences.

Figure 15:
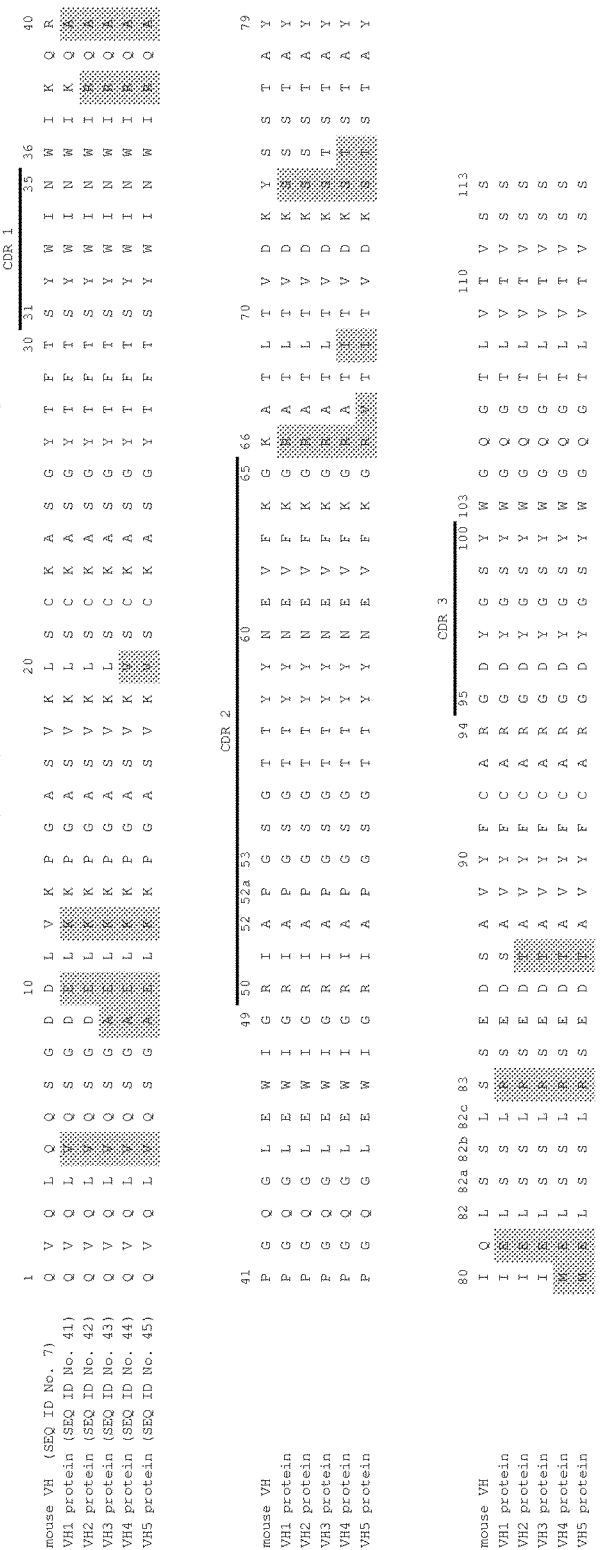

FIG. 15—Humanised 8H5 VH amino acid sequences.

Figure 16:
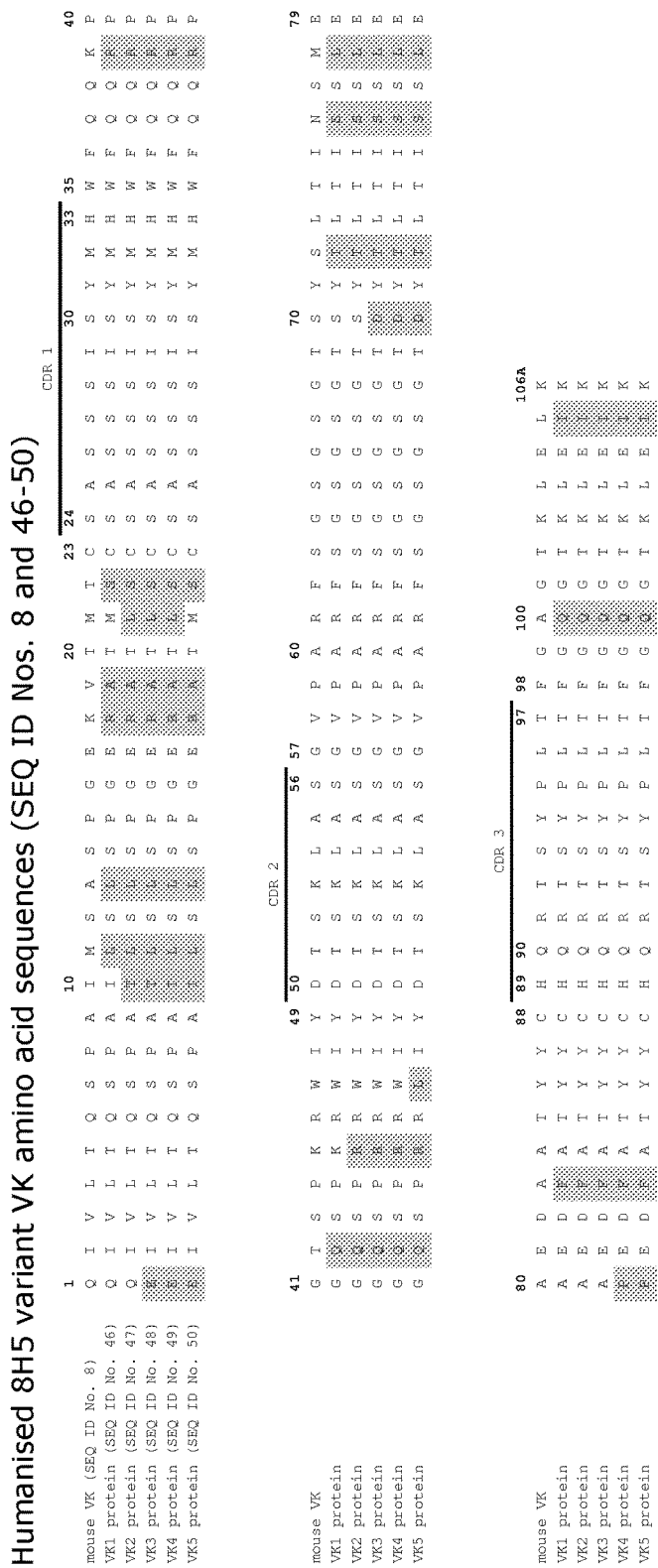

FIG. 16—Humanised 8H5 VK amino acid sequences.

Figure 17A:
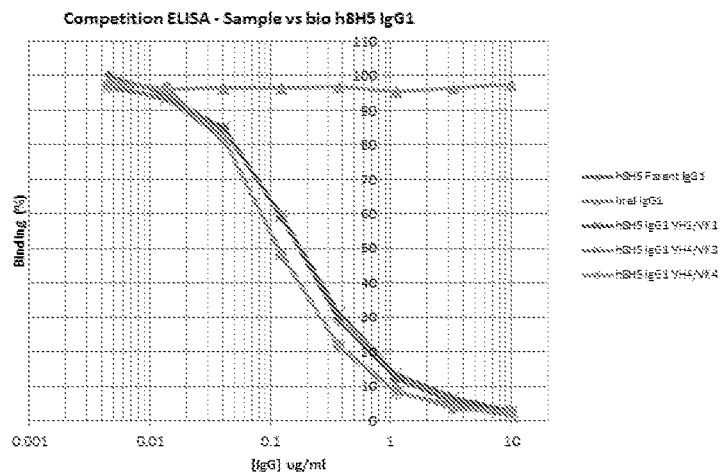
Figure 17B:
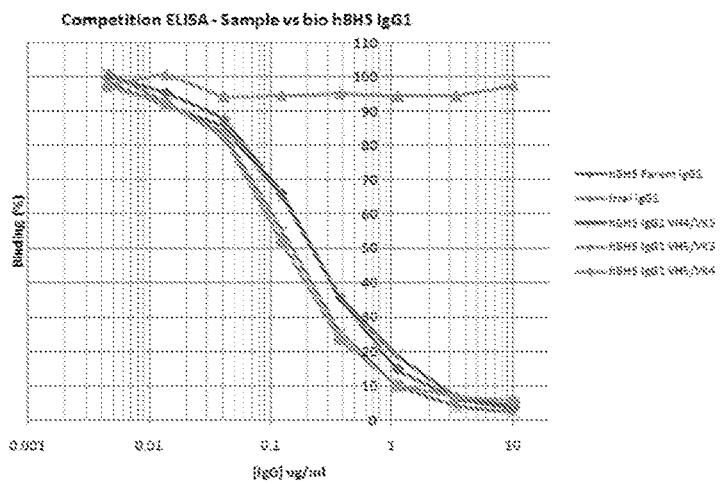
Figure 17C:
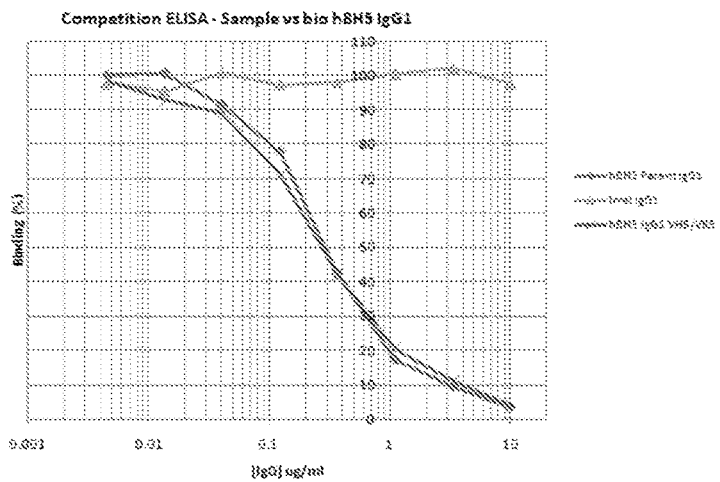
Figure 18A:
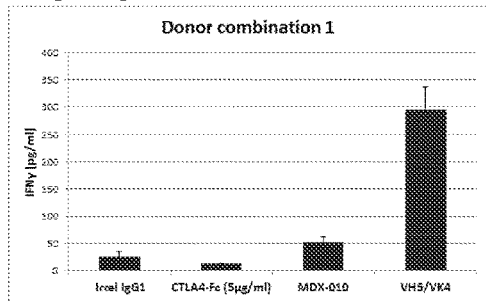
Figure 18B:
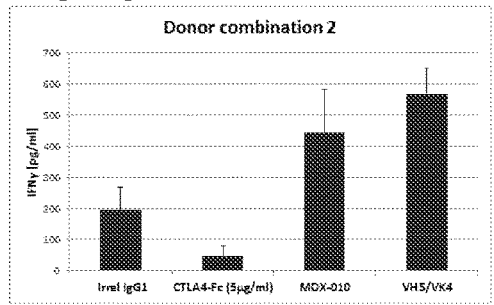
Figure 18C:
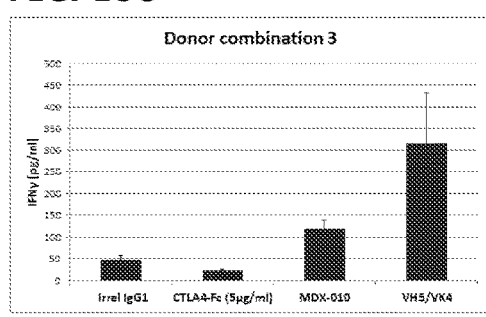
Figure 18D:
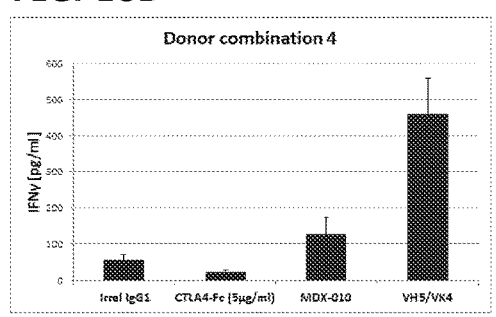
Figure 18E:
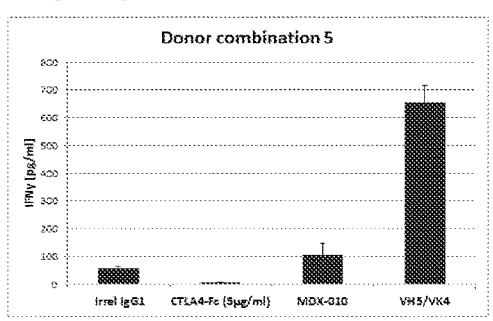
Figure 18F:
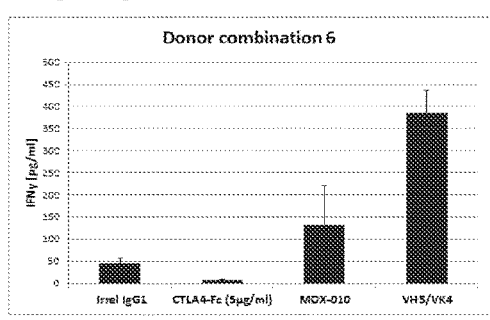

FIGS. 17A to 17C—Competition ELISA of humanised 8H5 antibodies for binding to CTLA4-Fc against biotinylated chimeric 8H5 human IgG1 (="h8H5 parent IgG1").

FIGS. 18A to 18F—IFN-γ secretion by lead humanised VH5/VK4 anti-CTLA4 and MDX0101 in a human mixed lymphocyte reaction with donor pairs 1 to 6, respectively.

Figure 19A:
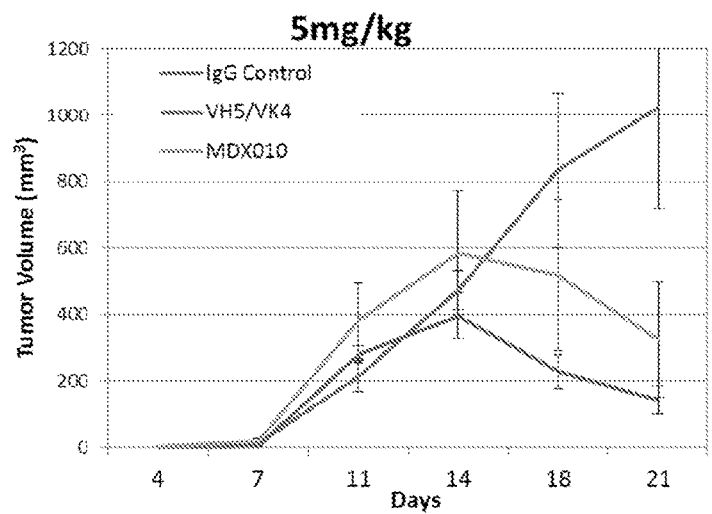
Figure 19B:
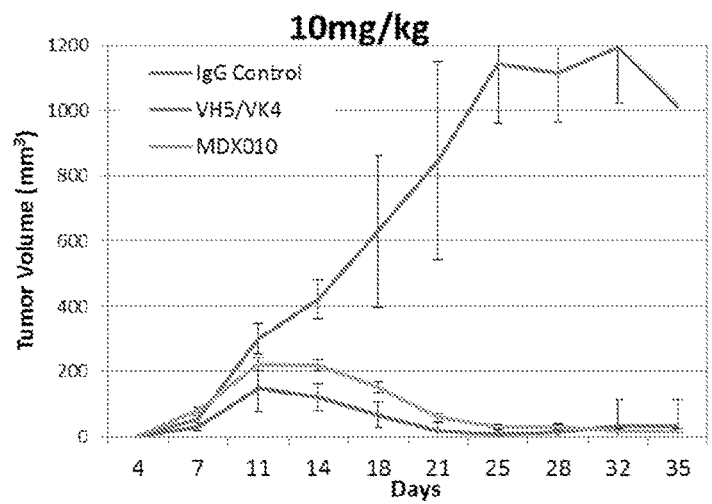

FIGS. 19A and 19B—Growth of MC38 tumour in human CTLA4 knock-in mice with weekly antibody doses (5 mg/kg in FIG. 19A and 10 mg/kg in FIG. 19B) starting at Day 2.

FIG. 20—Primer sequences for amplification of murine cDNA variable regions.

FIG. 21—Primer sequences for amplification of murine variable regions for cloning into pANT17 and pANT13.

Commercially available reagents referred to in the Examples were used according to manufacturer's instructions unless otherwise indicated. The source of cells identified in the Examples and throughout the specification by ECACC accession numbers is the European Collection of Cell Cultures (ECACC), Salisbury, England. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

Example 1

Generation of Mouse Monoclonal Antibodies

Recombinant CTLA4-fusion protein comprising the extracellular domain of human CTLA4 fused to the human IgG1 constant domain was purchased from R&D Systems (Oxford, UK). Extracellular CTLA4 fragment was prepared by proteolytic cleavage of the CTLA4-Fc fusion protein with Factor Xa (Qiagen, Crawley, UK) followed by subsequent removal of the protease using Factor Xa removal resin (Qiagen) and of the cleaved Fc fragment using Protein A-agarose to leave the CTLA4 extracellular domain only.

Female Balb/c mice were immunised subcutaneously with 200 ul of a 1:1 emulsion of Freunds Complete Adjuvant (Sigma-Aldrich, Dorset, UK) containing 20 ug of CTLA4-Fc fusion protein. Immunised mice were subsequently boosted approximately every 3 weeks with up to three intraperitoneal injections of a 1:1 emulsion of Freunds Incomplete Adjuvant (Sigma-Aldrich) containing 20 ug of CTLA4-Fc. 3 days prior to myeloma fusion, the two mice showing the highest antibody titre received an intrasplenic boost of either whole antigen or CTLA4 extracellular domain.

Spleens were extracted and homogenised to yield a single cell suspension. $1 \times 10^8$ spleen cells were fused with $5 \times 10^7$ NS0 mouse myeloma cells (2:1 ratio) using polyethylene glycol (PEG). The fused cells were resuspended in 200 ml of DMEM/20% FCS/5% BM Condimed H1 (Roche, Burgess Hill, UK) containing the hybridoma selection agents azaserine and hypoxanthine—"HAZA medium" and pipetted in 200 ul volumes into 10×96 well plates. Plates were incubated at 37° C. in 5% $CO_2$ and one half volume (100 ul) of each culture well was replaced every other day with fresh HAZA medium containing 2.5% BM Condimed H1. After 12 days incubation, 100 ul of spent medium from each growth well were transferred to a 96 well storage plate and tested for the presence of secreted anti-CTLA4-fusion protein antibodies using the CTLA4-fusion protein ELISA as described below. Immunopositive cultures were expanded by transferring to 1 ml of "H-medium" (DMEM/20% FCS/hypoxanthine) in a 24 well plate and growth allowed to proceed for 5-7 days. Positive cultures were then subcloned by limiting dilution, expanded and tested by CTLA4-fusion protein ELISA. In addition, positive cultures were tested by FACS as described below.

For limiting dilution, cells counts were determined using a haemocytometer and cells diluted serially in medium containing 2.5% BM Condimed H1 until cell densities of 5 to 15 cells/ml were achieved. For each hybridoma, 200 ul of cell solution was pipetted into 48 wells with a density of 1 to 3 cells per well. Cultures were maintained at 37° C. in 5% $CO_2$ for 2 weeks with an additional medium feed of half a volume after 1 week. Culture medium was tested for the presence of antibodies specific for anti-CTLA4-fusion protein by ELISA. ELISA positive clones were selected and expanded to 10 ml cultures in DMEM/20% FCS/2.5% BM Condimed H1. Clones were then frozen in medium containing 10% DMSO and stored in liquid N2, and also expanded further for antibody purification. Two hybridomas designated 3B10 and 8H5 were subcloned and subclones were then frozen and used for monoclonal antibody production in further studies.

To identify hybridomas secreting anti-human CTLA4-specific mouse antibodies, ELISA plates (VWR, Lutterworth, UK) were coated overnight at 4° C. with 100 ul/well of either recombinant CTLA4 fusion protein or human IgG1 (Sigma-Aldrich, Poole, UK) at 0.5 µg/ml in PBS. Plates were washed and blocked with 150 ul/well PBS containing 2% BSA. Cell culture supernatants or purified antibodies were diluted in PBS/2% BSA and 100 ul added to each plate followed by incubation for 1 hour at room temperature. Plates were washed three times with PBS-Tween (0.05%) and incubated for 1 hour with 100 ul/well goat anti-mouse Ig (Fab-specific) conjugated to Horseradish Peroxidase (Sigma-Aldrich). Plates were washed three times with PBS-Tween following which SigmaFast OPD substrate (Sigma-Aldrich) was added and incubated at room temperature in the dark for 4 minutes. The reaction was stopped by adding 50 µl of 3M HCl. Plates were read at 490 nm using a Dynex plate reader (Dynex, Worthing, UK).

Monoclonal antibodies were isotyped using the Rapid ELISA Mouse Antibody Isotyping Kit (Perbio, Cramlington, UK). Antibodies were purified on a 1 ml Protein A-sepharose column (GE Healthcare, Little Chalfont, UK). Prior to purification, both the tubing and the Protein A column were depyrogenated using 0.4M NaOH. The column was re-equilibrated with 20 CV of 1×PBS pH 7.4. Hybridoma cell culture supernatants were harvested, adjusted to 1×PBS pH 7.4 using 10×PBS and filter sterilised. Filtered supernatant was pumped through the column at 0.5 ml/min. The column was washed with 1×PBS pH 7.4 and IgG was eluted using sterile 0.1M Sodium Citrate pH3, with 0.9 ml fractions collected and neutralised with 0.1 ml of sterile 1M Tris-HCl pH 9. Under sterile conditions, the product was buffer exchanged into PBS pH 7.4 to remove any elution buffer and concentrate the sample. After concentration, antibodies were quantified by OD280 nm using an extinction coefficient, Ec (0.1%) of 1.4. Purified antibodies were analysed by SDS-PAGE using a Novex NuPAGE electrophoresis system with 4-12% NuPage gel (Invitrogen, Paisley, UK) and MES running buffer. 1 µg of antibody was prepared with 4× NuPAGE sample buffer plus beta-mercaptoethanol and heated. The gel was stained with InstantBlue staining solution (Expedeon, Cambridge, UK) and molecular size were estimated by comparing stained bands to PageRuler™ Plus Prestained Protein Ladder (Fermentas, York, UK). Two bands were identified for each antibody with no detectable contamination present.

In order to evaluate binding of antibodies to CTLA4 and blocking of the interaction between CTLA4 with CTLA4 ligands B7.1 and B7.2, competition assays were performed by ELISA. The ligands B7.1-Ig and B7.2-Ig (R&D Systems) were biotinylated using Biotin Tag™ Micro Biotinylation kit (Sigma-Aldrich). 96 well MaxiSorp plates (Nunc) were coated with 0.5 µg/ml recombinant human CTLA4-Ig (IgG1) (R&D Systems) in Dulbecco's PBS (PAA Laboratories, Yeovil, UK) (80 µl final volume) at 4° C. overnight. CTLA4-Ig was discarded and plates were blocked with Dulbecco's PBS-2% BSA for 1 hour at room temperature. Plates were washed 3 times with wash buffer (0.05% Tween20 in Dulbecco's-PBS). Test antibodies at various concentrations were premixed with either biotinylated-B7.1-Ig (0.36 µg/ml final concentration) or biotinylated-B7.2-Ig (0.65 µg/ml final concentration) and then added to the CTLA4-Ig plate (80 µl final volume). All samples were tested in duplicate. Plates were incubated 1 h at room temperature and washed 3 times with wash buffer. 80 µl of a 1 in 500 dilution of Streptavidin HRP (Sigma-Aldrich) was added and incubated for 1 hour at room temperature. Plates were washed 3 times with wash buffer and 80 µl of Sigma-Fast OPD substrate (Sigma-Aldrich, Cat# P9187) was added and incubated at room temperature in the dark for 4 minutes. The reaction was stopped by adding 50 µl of 3M HCl. Plates were read at 490 nm using Dynex plate reader. Subclones 8H5-1B1, 3B10-4F7, 7B9-1A3 and 2C7-1G10 were selected as producers of lead monoclonal antibodies based on binding to CTLA4 (FIG. 1). Of these leads, all but 7B9-1A3 were shown to compete with biotinylated B7.1 (FIG. 2) and biotinylated B7.2 (FIG. 3) for binding to human CTLA4.

In order to determine whether the lead monoclonal antibodies bound to CTLA4 expressed on the surface of T-cells, a flow cytometric analysis was performed. Human peripheral T cells were isolated from human PBMC (peripheral blood mononuclear cells) and stimulated to enhance expression of CTLA4. CD4+ cells were purified from PBMC using a CD4+ T Cell Isolation Kit (Miltenyi Biotec, Bisley, UK), plated out in a 24 well plate (1×10⁶ cells/well) in AIM-V Medium (Invitrogen, Paisley, UK) and incubated at 37° C. overnight. Cells were stimulated with Ionomycin (1 µg/ml) and PMA (phorbol 12-myristate 13-acetate) (50 ng/ml) and incubated 4 h at 37° C. Cells were washed once in AIM-V medium, fixed in PBS containing 2% formaldehyde for 15 min, and resuspended in FACS buffer (D-PBS containing 1% BSA, 0.05% sodium azide and 0.1% Saponin) at 2×10⁶ cells/ml and incubated 30 min at 4° C.

2×10⁵ cells were stained using either a 1 in 10 dilution of anti-CTLA4-PE conjugated antibody (BNI3) (Abcam, Cambridge, UK) as a positive control or with 5 µg/ml of individual anti-CTLA4 monoclonal antibodies together with a 1 in 50 dilution of anti-mouse IgG-PE conjugated antibody (Sigma). Mouse IgG (Sigma) was also included as separate controls for the different murine isotypes present within the lead monoclonal antibodies. Cells were stained for 1 hour at 4° C. An anti-mouse IgG-PE conjugated antibody only control was also included. Cells were washed twice with FACS buffer and optionally stained for 1 h in the dark at 4° C. with either a 1 in 40 dilution of mouse anti-human CD4-FITC conjugated antibody (Caltag, Buckingham, UK) or mouse IgG2a-FITC conjugated antibody (Caltag). After two washes with FACS buffer, cells were resuspended in FACS buffer and flow cytometry performed using a Beckton Dickinson FACSCalibur (Becton Dickinson, Oxford, UK). Instrument settings were determined by analysis of relevant isotype control antibodies. Based on the observed binding to CTLA4, monoclonal antibodies 8H5 and 3B10 were designated as primary and secondary lead monoclonal antibodies respectively.

Example 2

Variable Region Gene Sequencing

Subclones 3B10-4F7, 3B10-6E3, 8H5-1A1 and 8H5-1B1 producing the lead monoclonal antibodies 8H5 and 3B10 were subjected to variable region (V-region) sequence analysis. Total RNA was extracted from 3 to 10×10⁶ hybridoma cells using the RNAqueous-4PCR Kit (Ambion, Warrington, UK) and used to synthesis cDNA. Murine immunoglobulin heavy and kappa light chain V-region fragments were amplified by PCR using degenerate mouse leader sequence primers (Sigma) and unique constant domain primers (Sigma) as shown in FIG. 20. The resulting PCR fragments were subcloned into the pGEM-T Easy I vector system (Promega, Southampton, UK) and inserts were sequenced using the vector-specific primer, M13Forward (Sigma). All DNA sequencing was performed by Geneservice Ltd, Cambridge, UK. Unique V-region nucleotide sequences were obtained for 3B10 (SEQ ID Nos 1 and 2) and 8H5 (SEQ ID Nos 5 and 6). Sequences of 3B10 and 8H5 hypervariable regions (CDRs) were determined as follows;

| 3B10 | CDRH1 | DYNMD | SEQ ID No. 9 |
|------|-------|-------|--------------|
| 3B10 | CDRH2 | NINPNSESTSYNQKFKG | SEQ ID No. 10 |
| 3B10 | CDRH3 | DGNRYDAWFAY | SEQ ID No. 11 |
| 3B10 | CDRL1 | SASSSVTYMH | SEQ ID No. 12 |
| 3B10 | CDRL2 | STSILAS | SEQ ID No. 13 |
| 3B10 | CDRL3 | QQRTSYPLT | SEQ ID No. 14 |
| 8H5 | CDRH1 | SYWIN | SEQ ID No. 15 |
| 8H5 | CDRH2 | RIAPGSGTTYYNEVFKG | SEQ ID No. 16 |
| 8H5 | CDRH3 | GDYGSY | SEQ ID No. 17 |
| 8H5 | CDRL1 | SASSSISYMH | SEQ ID No. 18 |

| | -continued | |
|---|---|---|
| 8H5 | CDRL2 DTSKLAS | SEQ ID No. 19 |
| 8H5 | CDRL3 HQRTSYPLT | SEQ ID No. 20 |

Example 3

Generation of Chimeric Antibodies

The heavy and light chain variable domain sequences of the lead 3B10 and 8H5 monoclonal antibodies were PCR amplified and subcloned into pANT antibody expression vectors (FIGS. 8A-8B) with heavy and light chain V-regions cloned into pANT17 and pANT13 respectively. Heavy chain V-region genes were cloned into pANT17 via MluI and HindIII sites in frame with either the human γ1 heavy chain gene (G1m3 (G1m(f)) allotype) or the human γ4 heavy chain gene, and light chain V-region genes were cloned into pANT13 via BssHII and BamHI sites in frame with the human kappa light chain constant region gene (Km3 allotype). Transcription of both heavy and light chain genes was under the control of the CMV I/E promoter (U.S. Pat. No. 5,168,062 and U.S. Pat. No. 5,385,839, University of Iowa) and the pANT17 plasmid contained a mutant dhfr minigene (Simonsen & Levinson 1983, PNAS 80:2495-2499) under the control of a SV40 promoter and polyA sequence for selection in eukaryotic cells. Both pANT17 and pANT13 contained a β-lactamase ($Ap^R$) gene for prokaryotic selection and a pMB1 origin of replication for propagation in prokaryotic cells. All plasmids were propagated in E. coli XL1-blue (Stratagene Cat. No. 200130). Primers used to amplify the V-region genes for cloning into the pANT expression vectors are shown in FIG. 21.

The heavy and light chain expression constructs were then co-transfected either transiently into HEK293 cells by calcium phosphate-based transfection or stably transfected into NS0 cells by electroporation. Secreted antibody was purified from the cell culture supernatants by Protein A chromatography. By analysis with CTLA4 binding ELISA (FIG. 4), CTLA4 competition ELISA against B7.1 and B7.2 (FIGS. 5 and 6), and by binding to CTLA4 expressed on T cells by flow cytometry as in Example 1, both 3B10 and 8H5 chimeric antibodies were shown to retain the CTLA4 binding of the starting monoclonal antibodies.

Example 4

T-Cell Proliferation Assay

Figure 7B:
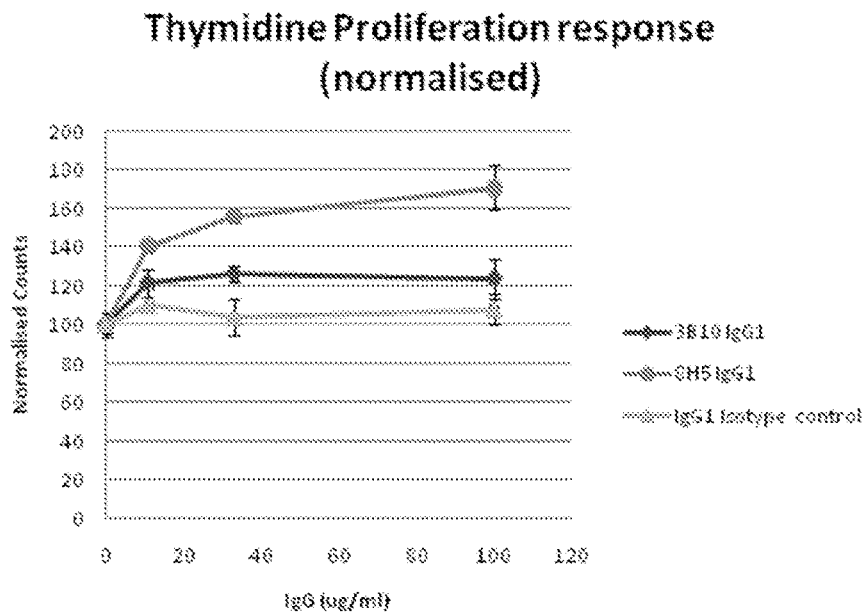

PBMC (peripheral blood mononuclear cells) were activated using beads coated with anti-human CD2, anti-human CD3 and anti-human CD28 antibodies (Miltenyi Biotec, Bisley, Surrey). $5 \times 10^5$ cells were plated out into each well of a 96-well plate in AIM-V medium with beads added to cells at a ratio of 1 bead per cell. Test or isotype control antibodies were diluted as appropriate in AIM-V medium and 50 μl per well added to the cells, giving a final volume of 200 μl. Medium only (no antibody) controls were also included. Plates were incubated for 4 days at 37° C. and cells were then pulsed with 0.75 μCi [3H]-Thymidine (Perkin Elmer, Beaconsfield, UK) in AIM-V® culture medium and incubated for a further 18 hours before harvesting onto filter mats (Perkin Elmer) using a TomTec Mach III (Hamden Conn., USA) cell harvester. Counts per minute (cpm) for each well were determined by Meltilex™ (Perkin Elmer) scintillation counting on a 1450 Microbeta Wallac Trilux Liquid Scintillation Counter (Perkin Elmer) in paralux, low background counting. Counts per minute for each antibody sample were normalised to the medium-only control. In two separate studies, chimeric antibodies were shown to reverse the CTLA4-induced inhibition of T cell proliferation as seen with the starting monoclonal antibodies (FIGS. 7A-7B).

Example 5

Generation of Humanised Antibodies

Humanised antibodies were generated using methods described in EP1844074 (Antitope Ltd). Structural models of the mouse V-regions were produced using Swiss PDB and analysed in order to identify important amino acids from the 3B10 and 8H5 V-regions that were likely to be important for the CTLA4 binding properties of the antibody ('constraining residues'). A database of human V-region sequences was used to identify segments of human V-region sequences containing each of the constraining residues to be used in design of the humanised antibodies. Typically two or more alternative V-region sequence segments were used to provide each constraining residue resulting in a large range of possible sequences of humanised anti-CTLA4 V-region sequences for both 8H5 and 3B10. These sequences were then analysed for the prediction of non-germline MHC class II peptide binding by in silico analysis as described in Fothergill et al. (WO9859244, Eclagen Ltd) and also for known CD4+ T-cell epitopes using databases including "The Immune Epitope Database and Analysis Resource", http: double slash www dot immuneepitope dot org slash. V-region sequences with predicted non-germline MHC class II binding peptides or with significant hits against T cell epitope databases were discarded. This resulted in a reduced set of V-region sequences. Selected combinations of V-region sequence segments were then combined to produce humanised heavy and light chain variable region amino acid sequences. Five heavy chains and five light chain sequences (designated VH1 to VH5, and VK1 to VK5 respectively) were selected for each of 8H5 (SEQ ID Nos 41 to 45 and 46 to 50 respectively) and 3B10 (SEQ ID Nos 31 to 35 and 36 to 40 respectively).

DNA encoding humanised variant V-regions was synthesised and subcloned into the expression vectors pANT17 and pANT13 as described in Example 3. All combinations of humanised VH and VK chains (i.e. a total of 25 pairings for each of 8H5 and 3B10) were transiently transfected into HEK293 and also transfected into NS0 cells, and antibody was purified by protein A chromatography from the culture supernatants as described in Example 3.

Example 6

Analysis of Humanised Antibodies

The binding of HEK-derived and NS0-derived 8H5 and 3B10 humanised variants to recombinant CTLA4 was assessed in a competition ELISA against the appropriate parent chimeric antibody. The parental 8H5 and 3B10 chimeric antibodies were biotinylated using Biotin Tag™ Micro Biotinylation kit (Sigma-Aldrich). 96 well MaxiSorp plates (Nunc) were coated with 0.5 μg/ml recombinant human CTLA4-Ig in Dulbecco's PBS (100 μl final volume) at 4° C. overnight. CTLA4-Ig was discarded and plates were blocked with Dulbecco's PBS-2% BSA for 1 hour at room temperature. Plates were washed 3 times with wash buffer (0.05% Tween20 in Dulbecco's-PBS). Test humanised antibodies at various concentrations were premixed with biotinylated parent chimeric antibody (0.02 µg/ml final concentration) and then added to the CTLA4-Ig plate (100 µl final volume). All samples were tested in duplicate. Plates were incubated for 1 h at room temperature and washed 3 times with wash buffer. 100 µl of a 1 in 500 dilution of Streptavidin HRP (Sigma-Aldrich) was added and incubated for 1 hour at room temperature. Plates were washed 3 times with wash buffer and 100 µl of SigmaFast OPD substrate (Sigma-Aldrich, Cat# P9187) was added and incubated at room temperature in the dark for 4 minutes. The reaction was stopped by adding 50 µl of 3M HCl. Plates were read at 490 nm using Dynex plate reader.

All lead 8H5 humanised variants displayed competitive binding profiles similar to the 8H5 chimeric antibody although variants containing the kappa chain VK5 showed slightly decreased binding compared to other variants (FIGS. 17A-17C). Similarly all lead humanised 3B10 variants displayed competitive binding profiles similar to the 3B10 chimeric antibody. In addition, all lead humanised 8H5 and 3B10 variants, when tested in the CTLA4 competition ELISA against B7.1 and B7.2 (Example 3) gave very similar competitive binding profiles to the chimeric antibody shown in FIGS. 5 and 6 whereby >90% of B7.1 or B7.2 binding was inhibited at the maximum concentrations of the lead humanised variants. A lead humanised variant VH5/VK4 (SEQ ID Nos 45 and 39 respectively) was chosen as the lead antibody for further studies.

Example 7

Generation of scFv's and Fab's

Humanised 8H5 and 3B10 variants from Example 6 were converted into scFv's and cloned into M13 phage display vectors as described in Benhar I. and Reiter Y., Current Protocols in Immunology, Unit 10.19B, Wiley Online Library, May 2002 (http: double slash www dot currentprotocols dot com slash protocol slash im1019b) using the pCANTAB5E vector RPAS Expression Module (Amersham Pharmacia Biotech, Little Chalfont, UK). Humanised VH and VK genes were amplified using primers which provided terminal SfiI and NotI restriction sites, an internal Gly4Ser linker and a C terminal his6 tag. The scFv constructs were inserted into the pCANTAB5E vector as SfiI-NotI fragments and transformed into *E. coli* HB2151 resulting in scFv exported to the periplasm and partially to the growth medium. scFv's were purified from growth medium by nickel-chelate affinity chromatography using HIS-Select HF Cartridges (Sigma-Aldrich). Purified scFv's were tested in B7.1-Ig and B7.2-Ig competition assay as detailed in Example 1 and all humanised scFvs exhibited competitive binding to CTLA4. Humanised 8H5 and 3B10 variants from Example 6 were also converted into Fab's using the method used for scFv's except that amplified humanised VH and VK genes were further amplified with CH1 and Cκ constant region genes to form VH-CH1 and VK-Cκ fragments which were further amplified with primers to join these fragments with a 22 amino acid pelB leader sequence (Lei S. P., Lin H. C., Wang S. S., Callaway J., and Wilcox G., J. Bacteriol. 169 (1987) p 4379-4383) between the upstream VH-CH1 and downstream VK-Cκ gene fragments resulting in a dicistronic Fab gene. Fab's from humanised antibody variants were generated and purified as above for scFv's and tested in B7.1-Ig and B7.2-Ig competition assay as detailed in Example 1. All humanised Fab's exhibited competitive binding to CTLA4.

Example 8

Analysis of CD4+ T Cell Responses

PBMCs were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMCs were isolated from buffy coats by Lymphoprep (Axis-shield, Dundee, UK) density centrifugation and $CD8^+$ T cells were depleted using $CD8^+$ RosetteSep™ (StemCell Technologies Inc, London, UK). Donors were characterised by identifying HLA-DR haplotypes using an HLA SSP-PCR based tissue-typing kit (Biotest, Solihull, UK). T cell responses to control antigens including the recall antigen tetanus toxin were also determined (KLH Pierce, Cramlingtom, UK and peptides derived from Influenza A and Epstein Barr viruses). PBMC were then frozen and stored in liquid nitrogen until required.

To prepare monocyte derived dendritic cells (DC), 50 different donor PBMCs were selected to provide a distribution with frequencies of HLA-DR and HLA-DQ allotypes similar to the frequencies in the overall world population. PBMCs were revived in AIM-V® culture medium and $CD14^+$ cells isolated using Miltenyi CD14 Microbeads and LS columns (Miltenyi Biotech, Oxford, UK). Monocytes were resuspended in AIM-V® supplemented with 1000 U/ml IL-4 and 1000 U/ml GM-CSF ("DC culture medium") to $4-6 \times 10^6$ PBMC/ml and then distributed in 24 well plates (2 ml final culture volume). Cells were fed on day 2 by half volume DC culture medium change. By day 3, monocytes had differentiated to semi-mature DC which were pre-incubated with either 40 ug/ml of test humanised or chimeric antibody, 100 µg/ml KLH or medium only. Semi-mature DC were incubated with antigen for 24 hours after which excess test antibody was removed by washing the cells twice and resuspending in DC culture medium supplemented with 50 ng/ml TNF-α (Peprotech, London, UK). DCs were fed on day 7 by a half volume DC culture medium (supplemented with 50 ng/ml TNFα) change before harvesting mature DC on day 8. The harvested mature DC were counted and viability assessed using trypan blue dye exclusion. The DC were then γ-irradiated (4000 rads) and resuspended at $2 \times 10^5$ cells per ml in AIM-V medium before use in the ELISpot and proliferation assays. Additionally, on day 8, fresh CD4+ T cells were also prepared. To purify CD4+ T cells, PBMCs were revived in AIM-V® culture medium and $CD4^+$ cells isolated using Miltenyi CD4 Microbeads and LS columns (Miltenyi Biotech, Oxford, UK) and resuspended in AIM-V® medium at $2 \times 10^6$ cells/ml.

On day 8, T cell proliferation assays were established whereby $1 \times 10^5$ autologous $CD4^+$ T cells were added to $1 \times 10^4$ humanised or chimeric antibody-loaded DC (ratio of 10:1) in 96 well U-bottomed plates, with AIM-V® medium added to a final volume 200 ul/well). On day 14, assay plates were pulsed with 1 uCi [3H] (Perkin Elmer, Beaconsfield, UK) per well in 25 ul AIMV for 6 hours before harvesting onto filter mats (Perkin Elmer) using a TomTec Mach III (Hamden Conn., USA) cell harvester. All antibody preparations were tested in sextuplet cultures. Counts per minute (cpm) for each well were determined by Meltilex™ (Perkin Elmer) scintillation counting on a 1450 Microbeta Wallac Trilux Liquid Scintillation Counter (Perkin Elmer) in paralux, low background counting. Counts per minute for each antibody sample were normalised to the AIM V® medium only control.

For ELISpot assays, ELISpot plates (Millipore, Watford, UK) were coated with 100 μl/well IL-2 capture antibody (R&D Systems, Abingdon, UK) in PBS. Plates were then washed twice in PBS, incubated overnight in block buffer (1% BSA (Sigma) in PBS) and washed in AIM V® medium. On day 8, $1 \times 10^5$ autologous CD4+ T cells were added to $1 \times 10^4$ antigen loaded DC (ratio of 10:1) in 96 well ELISpot plates. All antibody preparations were tested in sextuplet cultures. For each donor PBMC, a negative control (AIM V® medium alone), no cells control and a PHA (10 ug/ml) positive control were also included.

After a further 7 day incubation period, ELISpot plates were developed by three sequential washes in $dH_2O$ and PBS prior to the addition of 100 μl filtered biotinylated detection antibody (R&D Systems, Abingdon, UK) in PBS/ 1% BSA. Following incubation at 37° C. for 1.5 hour, plates were further washed three times in PBS and 100 μl filtered streptavidin-AP (R&D Systems) in PBS/1% BSA was added for 1 hour (incubation at room temperature). Streptavidin-AP was discarded and plates were washed four times in PBS. BCIP/NBT (R&D Systems) was added to each well and incubated for 30 minutes at room temperature. Spot development was stopped by washing the wells and the backs of the wells three times with $dH_2O$. Dried plates were scanned on an Immunoscan™ Analyser and spots per well (spw) were determined using Immunoscan™ Version 4 software.

For both proliferation and IL-2 ELISpot assays, results were expressed as a Stimulation Index (SI) defined as the ratio of cpm (proliferation assay) or spots (ELISpot assay) for the test antibody against a medium-only control using a threshold of SI equal to or greater than 2 (SI≥2.0) for positive T cell responses. The data showed that the chimeric 8H5 and chimeric 3B10 antibodies induced T cell responses in 8 or more of the 50 donor PBMCs tested (>=16%) whilst none of the humanised 8H5 or 3B10 antibodies induced T cell responses in more than 2 of 50 donors (<=4%, average 2%+−2%) demonstrating the effectiveness of the humanisation process in removing T cell responses from the V-regions. In parallel, DNA with V-region sequences from the fully human anti-CTLA4 antibodies MDX010 (Ipilimumab) (Keler et al., ibid) and Tremelimumab (Ribas et al., ibid) were synthesised and used to produce recombinant IgG1/ kappa forms of these antibodies with methods as detailed in Example 5. NS0-derived preparations of these antibodies were then tested with the same 50 donor PBMCs as above for induction of CD4+ helper T cell responses in sextuplicate cultures. T cell responses were detected in an average of 4 donors for Ipilimumab (8%+−2%) and 5 donors for the IgG1/κ version of Tremelimumab (10%+−2%) thus demonstrating that only the humanised anti-CTLA4 antibodies of the present invention, when tested in vitro for induction of CD4+ helper T cell responses in 50 human blood samples, were able to give CD4+ T cell responses in <=4% of donors.

Example 9

Human Mixed Lymphocyte Reaction (MLR) Model

A mixed lymphocyte reaction assay was used to measure the effect of blocking the CTLA4 pathway on IFN-γ secretion as a measure of human T cell activation. Fresh blood from multiple human donors (obtained from UK National Blood Transfusion Service, Example 8) was diluted 1:1 with PBS/2% human serum and layered on Lymphoprep solution (Nycomed) for centrifugation at 900 g. PBMCs were removed from the interface, washed and resuspended in AIM-V medium (Invitrogen). PBMCs generated from different mismatched donor pairs were then combined at a 1:1 ratio and plated in a 96 well plate to provide a total of $2.5 \times 10^5$ PBMCs per sample well. PHA (phytohemaglutinin, Sigma Aldrich) was added for a final concentration of 2 μg/ml to stimulate proliferation of T-cell populations. Either the lead VH5/VK4 anti-CTLA4 antibody, the MDX010 anti-CTLA4 control antibody (Example 8) or an isotype control IgG1 antibody were added to a final concentration of 150 μg/ml. 5 μg/ml CTLA4-Fc was also used instead of antibody as a control to demonstrate inhibition of IFN-γ secretion. Total final volume per well was 1500 and each antibody was tested five times per donor combination. 96 well plates were incubated under normal culture conditions for 72 hrs after which 100 μl supernatant was sampled for measurement of IFN-γ by ELISA (Thermo scientific, ESS0002) following the manufacturer's recommended protocol. From the data in FIGS. 19A-19B, the lead VH5/VK4 antibody showed higher T cell activation than the MDX010 anti-CTLA4 control antibody for all donor combinations with an average increase of >2-fold in T cell activation for VH5/VK4 compared to MDX010.

Example 10

Tumour Animal Model

A tumour animal model was used for the in vivo analysis of anti-human CTLA4 antibodies in inhibiting tumour growth. In the model, MC38 murine colon tumour cells (Corbett et al., (1975) Cancer Res 35:2434-2439, supplied by OncoImmune, Inc., Ann Arbor, USA) were grown in human CTLA4 knock-in mice (OncoImmune, Inc.).

CTLA4 knock-in mice (7-10 weeks old, males and females distributed equally across groups) were injected subcutaneously in the flank with $5 \times 10^5$ MC38 tumour cells in 0.1 ml volume. Either the lead VH5/VK4 anti-CTLA4 antibody, MDX010 (Example 8) or an isotype matched control antibody were injected at either 5 mg/kg or 10 mg/kg doses (dosing volume 10 ml/kg) weekly starting the day following tumour cell administration ("Day 2"). Tumour measurements were taken biweekly during the course of the experiment by caliper measurement and tumour size was expressed as the cubic volume ($mm^3$). Animals were followed either until a tumour volume of 2000 $mm^3$ was reached or at day 45 after injection of tumour cells. The results shown in Example 19 demonstrate an improved inhibition of tumour growth by the lead VH5/VK4 anti-CTLA4 antibody compared to MDX010.

The invention claimed is:

1. An anti-CTLA4 humanised antibody comprising variable regions having CDR sequences of:
   - (i) CDRH1 comprising sequence DYNMD (SEQ ID NO: 9),
   - (ii) CDRH2 comprising sequence NINPNSESTSYNQKFKG (SEQ ID NO: 10),
   - (iii) CDRH3 comprising sequence DGNRYDAWFAY (SEQ ID NO: 11),
   - (iv) CDRL1 comprising sequence SASSSVTYMH (SEQ ID NO: 12),
   - (v) CDRL2 comprising sequence STSILAS (SEQ ID NO: 13), and
   - (vi) CDRL3 comprising sequence QQRTSYPLT (SEQ ID NO: 14);

or
   - (i) CDRH1 comprising sequence SYWIN (SEQ ID NO: 15),
   - (ii) CDRH2 comprising sequence RIAPGSGTTYY-NEVFKG (SEQ ID NO: 16),
   - (iii) CDRH3 comprising sequence GDYGSY (SEQ ID NO: 17),
   - (iv) CDRL1 comprising sequence SASSSISYMH (SEQ ID NO: 18),
   - (v) CDRL2 comprising sequence DTSKLAS (SEQ ID NO: 19), and
   - (vi) CDRL3 comprising sequence HQRTSYPLT (SEQ ID NO: 20).

2. The antibody of claim 1 comprising variable region sequences selected from the group consisting of SEQ ID NOS: 31-35 for the heavy chain variable region in combination with sequences selected from the group consisting of SEQ ID NOS: 36-40 for the light chain variable region.

3. The antibody of claim 1 comprising variable region sequences selected from the group consisting of SEQ ID NOS: 41-45 for the heavy chain variable region in combination with sequences selected from the group consisting of SEQ ID NOS: 46-50 for the light chain variable region.

4. The antibody of claim 3 comprising SEQ ID NO: 45 for the heavy chain variable region in combination with SEQ ID NO: 49 for the light chain variable region.

5. The antibody of claim 1 which, when tested in vitro for induction of CD4+ helper T cell responses in at least 50 human blood samples with a distribution of HLA-DR allotypes from the human population, gives rise to <=4% of T cell responses.

6. The antibody of claim 1 wherein the variable region sequences are entirely composed of sequences from human antibody variable regions.

7. The antibody of claim 1 wherein binding to human CTLA4 can block binding to human B7.1 or B7.2 by at least 90%.

8. The antibody of claim 1 which binds to human CTLA4 with an equilibrium dissociation constant (Kd) of $10^{-8}$M or less.

9. The antibody of claim 1 which is comprised of variable regions together with a heavy chain constant region of isotype IgG1, IgG2, IgG3 or IgG4, and a light chain constant region of isotype kappa.

10. The antibody of claim 9 where the human constant regions are IgG1 and kappa, or IgG4 and kappa.

11. The antibody of claim 1 where the antibody is a scFv or Fab.

12. A multispecific antibody comprising one or more antibodies of claim 1.

13. A polynucleotide encoding an anti-CTLA4 humanised antibody of claim 1.

14. A vector comprising the polynucleotide of claim 13.

15. A cultured host cell comprising a vector of claim 14.

16. A composition comprising an anti-CTLA4 humanised antibody of claim 1 or a polynucleotide encoding the antibody.

17. A method for treating a disease including cancer or a cell proliferative disorder comprising administering an effective amount of an anti-CTLA4 humanised antibody of claim 1 or a polynucleotide encoding the antibody to a subject in need of such treatment.

18. The method of claim 17 which further comprises co-administering an effective amount of a chemotherapeutic agent.

19. The method of claim 17 which further comprises co-administering a pharmaceutical carrier including a vaccine.

* * * * *

SEQUENCE LISTING

<160> NUMBER OF SEQ ID NOS: 50

<210> SEQ ID NO 1
<211> LENGTH: 360
<212> TYPE: DNA

<213> ORGANISM: Mus musculus
<220> FEATURE:
<223> OTHER INFORMATION: 3B10 Mouse VH

<400> SEQUENCE: 1

| | | | | | |
|---|---|---|---|---|---|
| gaggtccagc | tgcaacagtt | tggagctgaa | ctggtgaagc | ctggggcttc | agtgaagatg | 60 |
| tcctgcaagg | cttctggcta | cacattcact | gactacaaca | tggactgggt | gaggcagagc | 120 |
| catggaaaga | gtcttgagtg | gatcggaaat | attaatccta | actctgagag | tactagttac | 180 |
| aaccagaagt | tcaagggaaa | ggccacattg | actgtagaca | agtcctccag | cacagcctac | 240 |
| atggagctcc | gcagcctgac | atctgatgac | actgcagtct | attactgtac | aagagacggg | 300 |
| aataggtacg | acgcctggtt | tgcttactgg | ggccaaggga | ctctggtcac | tgtctcctca | 360 |

<210> SEQ ID NO 2
<211> LENGTH: 318
<212> TYPE: DNA
<213> ORGANISM: Mus musculus
<220> FEATURE:
<223> OTHER INFORMATION: 3B10 Mouse VK

<400> SEQUENCE: 2

| | | | | | |
|---|---|---|---|---|---|
| cagattgttc | tcacccagtc | tccagcaatc | atgtctgcat | ctccagggga | gaaggtcacc | 60 |
| atgacctgca | gtgccagctc | aagtgttact | tacatgcact | ggttccagca | gaagccaggc | 120 |
| acttctccca | aactctggat | ttatagcaca | tccatcctgg | cttctggagt | ccctgctcgc | 180 |
| ttcagtggca | gtggatctgg | gacctcttac | tctctcacaa | tcagccgaat | ggaggctgaa | 240 |
| gatgctgcca | cttattactg | ccagcaaagg | actagttacc | cgctcacgtt | cggtactggg | 300 |
| accaagctgg | agctgaaa | | | | | 318 |

<210> SEQ ID NO 3
<211> LENGTH: 120
<212> TYPE: PRT
<213> ORGANISM: Mus musculus
<220> FEATURE:
<223> OTHER INFORMATION: 3B10 Mouse VH

<400> SEQUENCE: 3

Glu Val Gln Leu Gln Gln Phe Gly Ala Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met Asp Trp Val Arg Gln Ser His Gly Lys Ser Leu Glu Trp Ile
        35                  40                  45

Gly Asn Ile Asn Pro Asn Ser Glu Ser Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Asp Asp Thr Ala Val Tyr Tyr Cys
                85                  90                  95

Thr Arg Asp Gly Asn Arg Tyr Asp Ala Trp Phe Ala Tyr Trp Gly Gln
            100                 105                 110

Gly Thr Leu Val Thr Val Ser Ser
        115                 120

<210> SEQ ID NO 4
<211> LENGTH: 106
<212> TYPE: PRT
<213> ORGANISM: Mus musculus

```
<220> FEATURE:
<223> OTHER INFORMATION: 3B10 Mouse VK

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Phe Gln Gln Lys Pro Gly Thr Ser Pro Lys Leu Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Thr Ser Tyr Pro Leu Thr
                85                  90                  95

Phe Gly Thr Gly Thr Lys Leu Glu Leu Lys
            100                 105

<210> SEQ ID NO 5
<211> LENGTH: 345
<212> TYPE: DNA
<213> ORGANISM: Mus musculus
<220> FEATURE:
<223> OTHER INFORMATION: 8H5 Mouse VH

<400> SEQUENCE: 5
caggtccagc tgcaacagtc tggagatgat ctggtaaagc ctggggcctc agtgaagctg      60
tcctgcaagg cttctggcta caccttcacc agctactgga ttaactggat aaaacagagg     120
cctggacagg gccttgagtg gataggacgt attgctcctg aagtggtac tacttactac      180 aatgaagtgt tcaagggcaa ggcaacactg actgtagaca atattccag cacagcctac      240 attcagctca gcagcctgtc atctgaggac tctgctgtct atttctgtgc aagaggggac      300
tatggttctt actggggcca agggactctg gtcactgtct cctca                     345

<210> SEQ ID NO 6
<211> LENGTH: 318
<212> TYPE: DNA
<213> ORGANISM: Mus musculus
<220> FEATURE:
<223> OTHER INFORMATION: 8H5 Mouse VK

<400> SEQUENCE: 6
caaattgttc tcacccagtc tccagcaatc atgtctgcat ctccagggga gaaggtcacc      60
atgacctgca gtgccagctc aagtataagt tacatgcact ggttccagca gaagccaggc     120
acctccccca aaagatggat ttatgacaca tccaaactgg cttctggagt ccctgctcgc     180
ttcagtggca gtgggtctgg gacctcttat tctctcacaa tcaacagcat ggaggctgaa     240
gatgctgcca cttattactg ccatcagcgg actagttacc cactcacgtt cggtgctggg     300
accaagctgg agctgaaa                                                   318

<210> SEQ ID NO 7
<211> LENGTH: 115
<212> TYPE: PRT
<213> ORGANISM: Mus musculus
<220> FEATURE:
<223> OTHER INFORMATION: 8H5 Mouse VH

<400> SEQUENCE: 7
```

```
Gln Val Gln Leu Gln Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Lys Ala Thr Leu Thr Val Asp Lys Tyr Ser Ser Thr Ala Tyr
65                  70                  75                  80

Ile Gln Leu Ser Ser Leu Ser Ser Glu Asp Ser Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 8
<211> LENGTH: 106
<212> TYPE: PRT
<213> ORGANISM: Mus musculus
<220> FEATURE:
<223> OTHER INFORMATION: 8H5 Mouse VK

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Phe Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Asn Ser Met Glu Ala Glu
65                  70                  75                  80

Asp Ala Ala Thr Tyr Tyr Cys His Gln Arg Thr Ser Tyr Pro Leu Thr
                85                  90                  95

Phe Gly Ala Gly Thr Lys Leu Glu Leu Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: 3B10 VH CDR1 Peptide

<400> SEQUENCE: 9

Asp Tyr Asn Met Asp
1               5

<210> SEQ ID NO 10
<211> LENGTH: 17
<212> TYPE: PRT
<213> ORGANISM: Artificial Sequence
<220> FEATURE:
<223> OTHER INFORMATION: 3B10 VH CDR2 Peptide

<400> SEQUENCE: 10
```

```
Asn Ile Asn Pro Asn Ser Glu Ser Thr Ser Tyr Asn Gln Lys Phe Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: 3B10 VH CDR3 Peptide

<400> SEQUENCE: 11

Asp Gly Asn Arg Tyr Asp Ala Trp Phe Ala Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: 3B10 VK CDR1 Peptide

<400> SEQUENCE: 12

Ser Ala Ser Ser Ser Val Thr Tyr Met His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: 3B10 VK CDR2 Peptide

<400> SEQUENCE: 13

Ser Thr Ser Ile Leu Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: 3B10 VK CDR3 Peptide

<400> SEQUENCE: 14

Gln Gln Arg Thr Ser Tyr Pro Leu Thr
1               5

<210> SEQ ID NO 15
<211> LENGTH: 5
<212> TYPE: PRT
<213> ORGANISM: Artificial Sequence
<220> FEATURE:
<223> OTHER INFORMATION: 8H5 VH CDR1 Peptide

<400> SEQUENCE: 15

Ser Tyr Trp Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: 8H5 VH CDR2 Peptide

<400> SEQUENCE: 16
```

Arg Ile Ala Pro Gly Ser Gly Thr Thr Tyr Tyr Asn Glu Val Phe Lys
1               5                   10                  15

Gly

<210> SEQ ID NO 17
<211> LENGTH: 6
<212> TYPE: PRT
<213> ORGANISM: Artificial Sequence
<220> FEATURE:
<223> OTHER INFORMATION: 8H5 VH CDR3 Peptide

<400> SEQUENCE: 17

Gly Asp Tyr Gly Ser Tyr
1               5

<210> SEQ ID NO 18
<211> LENGTH: 10
<212> TYPE: PRT
<213> ORGANISM: Artificial Sequence
<220> FEATURE:
<223> OTHER INFORMATION: 8H5 VK CDR1 Peptide

<400> SEQUENCE: 18

Ser Ala Ser Ser Ser Ile Ser Tyr Met His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: 8H5 VK CDR2 Peptide

<400> SEQUENCE: 19

Asp Thr Ser Lys Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: 8H5 VK CDR3 Peptide

<400> SEQUENCE: 20

His Gln Arg Thr Ser Tyr Pro Leu Thr
1               5

<210> SEQ ID NO 21
<211> LENGTH: 345
<212> TYPE: DNA
<213> ORGANISM: Artificial Sequence
<220> FEATURE:
<223> OTHER INFORMATION: 8H5 Humanised VH Variant 1 Synthetic DNA

<400> SEQUENCE: 21
caagtgcagc tggtgcagtc tggcgacgag ctgaagaaac ctggcgcctc cgtgaagctg      60
tcctgcaagg cctccggcta caccttcacc agctactgga ttaactggat caagcaggcc     120
cctgggcagg gcctggaatg gatcggcaga atcgcccctg gctccggcac cacctactac     180
aacgaggtgt tcaagggcag agccaccctg accgtggaca gtcctcctc caccgcctac     240 atcgagctgt cctccctgcg gagcgaggat tccgccgtgt acttctgcgc cagaggcgac     300
tacggctcct actggggcca gggcaccctg gtcaccgtgt catca                     345

<210> SEQ ID NO 22
<211> LENGTH: 345
<212> TYPE: DNA
<213> ORGANISM: Artificial Sequence
<220> FEATURE:
<223> OTHER INFORMATION: 8H5 Humanised VH Variant 2 Synthetic DNA

<400> SEQUENCE: 22

```
caagtgcagc tggtgcagtc tggcgacgag ctgaagaaac ctggcgcctc cgtgaagctg      60
tcctgcaagg cctccggcta caccttcacc agctactgga tcaactggat ccggcaggcc     120
cctgggcagg gcctggaatg gatcggcaga atcgcccctg gctccggcac cacctactac     180
aacgaggtgt tcaagggcag agccaccctg accgtggaca gtcctcctc caccgcctac     240 atcgagctgt cctccctgcg gagcgaggat accgccgtgt acttctgcgc cagaggcgac     300
tacggctcct actggggcca gggcaccctg gtcaccgtgt catca                     345
```

<210> SEQ ID NO 23
<211> LENGTH: 345
<212> TYPE: DNA
<213> ORGANISM: Artificial Sequence
<220> FEATURE:
<223> OTHER INFORMATION: 8H5 Humanised VH Variant 3 Synthetic DNA

<400> SEQUENCE: 23

```
caagtgcagc tggtgcagtc tggcgccgag ctgaagaaac ctggcgcctc cgtgaagctg      60
tcctgcaagg cctccggcta caccttcacc agctactgga tcaactggat ccggcaggcc     120
cctgggcagg gcctggaatg gatcggcaga atcgcccctg gctccggcac cacctactac     180
aacgaggtgt tcaagggcag agccaccctg accgtggaca gtccacctc caccgcctac     240 atcgagctgt cctccctgcg gagcgaggat accgccgtgt acttctgcgc cagaggcgac     300
tacggctcct actggggcca gggcaccctg gtcaccgtgt catca                     345
```

<210> SEQ ID NO 24
<211> LENGTH: 345
<212> TYPE: DNA
<213> ORGANISM: Artificial Sequence
<220> FEATURE:
<223> OTHER INFORMATION: 8H5 Humanised VH Variant 4 Synthetic DNA

<400> SEQUENCE: 24

```
caagtgcagc tggtgcagtc tggcgccgag ctgaagaaac ctggcgcctc cgtgaaggtg      60
tcctgcaagg cctccggcta caccttcacc agctactgga tcaactggat ccggcaggcc     120
cctgggcagg gcctggaatg gatcggcaga atcgcccctg gctccggcac cacctactac     180
aacgaggtgt tcaagggcag agccaccatc accgtggaca gtccacctc caccgcctac     240 atggagctgt cctccctgcg gagcgaggat accgccgtgt acttctgcgc cagaggcgac     300
tacggctcct actggggcca gggcaccctg gtcaccgtgt catca                     345
```

<210> SEQ ID NO 25
<211> LENGTH: 345
<212> TYPE: DNA
<213> ORGANISM: Artificial Sequence
<220> FEATURE:
<223> OTHER INFORMATION: 8H5 Humanised VH Variant 5 Synthetic DNA

<400> SEQUENCE: 25

```
caagtgcagc tggtgcagtc tggcgccgag ctgaagaaac ctggcgcctc cgtgaaggtg      60
```

-continued
tcctgcaagg cctccggcta caccttcacc agctactgga tcaactggat ccggcaggcc 120
cctgggcagg gcctggaatg gatcggcaga atcgcccctg gctccggcac cacctactac 180
aacgaggtgt tcaagggcag agtgaccatc accgtggaca agtccacctc caccgcctac 240
atggagctgt cctccctgcg gagcgaggat accgccgtgt acttctgcgc cagaggcgac 300
tacggctcct actggggcca gggcaccctg gtcaccgtgt catca 345

<210> SEQ ID NO 26
<211> LENGTH: 321
<212> TYPE: DNA
<213> ORGANISM: Artificial Sequence
<220> FEATURE:
<223> OTHER INFORMATION: 8H5 Humanised VK Variant 1 Synthetic DNA

<400> SEQUENCE: 26
caaatcgtgc tgacccagtc ccccgccatc ctgtctctga gccctggcga gcgggccaca 60
atgagctgct ccgcctcctc cagcatctcc tacatgcact ggttccagca gcggcctggc 120
cagtctccta agcggtggat ctacgacacc tccaagctgg cctccggcgt gcccgccaga 180
ttctctggct ccggctccgg cacctcctac accctgacaa tctccagcct ggaagccgag 240
gacttcgcca cctactactg ccaccagcgg accagctacc ccctgacctt cggccagggc 300
accaagctgg aaatcaaacg t 321

<210> SEQ ID NO 27
<211> LENGTH: 321
<212> TYPE: DNA
<213> ORGANISM: Artificial Sequence
<220> FEATURE:
<223> OTHER INFORMATION: 8H5 Humanised VK Variant 2 Synthetic DNA

<400> SEQUENCE: 27
cagatcgtgc tgacccagtc ccccgccacc ctgtctctga gccctggcga gagagccacc 60
ctgagctgct ccgcctcctc cagcatctcc tacatgcact ggttccagca gcggcctggc 120
cagtctcctc ggcggtggat ctacgacacc tccaagctgg cctccggcgt gcccgccaga 180
ttctctggct ccggctccgg cacctcctac accctgacaa tctccagcct ggaagccgag 240
gacttcgcca cctactactg ccaccagcgg accagctacc ccctgacctt cggccagggc 300
accaagctgg aaatcaaacg t 321

<210> SEQ ID NO 28
<211> LENGTH: 321
<212> TYPE: DNA
<213> ORGANISM: Artificial Sequence
<220> FEATURE:
<223> OTHER INFORMATION: 8H5 Humanised VK Variant 3 Synthetic DNA

<400> SEQUENCE: 28
gaaatcgtgc tgacccagtc ccccgccacc ctgtctctga gccctggcga gagagccacc 60
ctgagctgct ccgcctcctc cagcatctcc tacatgcact ggttccagca gcggcctggc 120
cagtctcctc ggcggtggat ctacgacacc tccaagctgg cctccggcgt gcccgccaga 180
ttctctggct ccggctccgg caccgactac accctgacaa tctccagcct ggaagccgag 240
gacttcgcca cctactactg ccaccagcgg accagctacc ccctgacctt cggccagggc 300
accaagctgg aaatcaaacg t 321

<210> SEQ ID NO 29
<211> LENGTH: 321

```
<212> TYPE: DNA
<213> ORGANISM: Artificial Sequence
<220> FEATURE:
<223> OTHER INFORMATION: 8H5 Humanised VK Variant 4 Synthetic DNA

<400> SEQUENCE: 29
gaaatcgtgc tgacccagtc cccgccacc  ctgtctctga gccctggcga gagagccacc      60
ctgagctgct ccgcctcctc cagcatctcc tacatgcact ggttccagca gcggcctggc     120
cagtctcctc ggcggtggat ctacgacacc tccaagctgg cctccggcgt gcccgccaga     180
ttctctggct ccggctccgg caccgactac accctgacaa tctccagcct ggaacccgag     240
gacttcgcca cctactactg ccaccagcgg accagctacc ccctgacctt cggccagggc     300
accaagctgg aaatcaaacg t                                               321

<210> SEQ ID NO 30
<211> LENGTH: 321
<212> TYPE: DNA
<213> ORGANISM: Artificial Sequence
<220> FEATURE:
<223> OTHER INFORMATION: 8H5 Humanised VK Variant 5 Synthetic DNA

<400> SEQUENCE: 30
gaaatcgtgc tgacccagtc cccgccacc  ctgtctctga gccctggcga gcgggccaca      60
atgagctgct ccgcctcctc cagcatctcc tacatgcact ggttccagca gcggcctggc     120
cagtctcctc ggcggctgat ctacgacacc tccaagctgg cctccggcgt gcccgccaga     180
ttctctggct ccggctccgg caccgactac accctgacaa tctccagcct ggaacccgag     240
gacttcgcca cctactactg ccaccagcgg accagctacc ccctgacctt cggccagggc     300
accaagctgg aaatcaaacg t                                               321

<210> SEQ ID NO 31
<211> LENGTH: 120
<212> TYPE: PRT
<213> ORGANISM: Artificial Sequence
<220> FEATURE:
<223> OTHER INFORMATION: 3B10 Humanised VH1 Peptide

<400> SEQUENCE: 31

Glu Val Gln Leu Val Gln Ser Gly Ala Glu Leu Lys Lys Pro Gly Ala
1               5                   10                  15

Ser Val Lys Met Ser Cys Lys Ala Ser Gly Tyr Thr Phe Thr Asp Tyr
            20                  25                  30

Asn Met Asp Trp Val Arg Gln Ala His Gly Lys Gly Leu Glu Trp Ile
        35                  40                  45

Gly Asn Ile Asn Pro Asn Ser Glu Ser Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Asp Gly Asn Arg Tyr Asp Ala Trp Phe Ala Tyr Trp Gly Gln
                100                 105                 110

Gly Thr Leu Val Thr Val Ser Ser
        115                 120

<210> SEQ ID NO 32
<211> LENGTH: 120
<212> TYPE: PRT
```

```
<213> ORGANISM: Artificial Sequence
<220> FEATURE:
<223> OTHER INFORMATION: 3B10 Humanised VH2 Peptide

<400> SEQUENCE: 32

Gln Val Gln Leu Val Gln Ser Gly Ala Glu Leu Lys Lys Pro Gly Ala
1               5                   10                  15

Ser Val Lys Met Ser Cys Lys Ala Ser Gly Tyr Thr Phe Thr Asp Tyr
            20                  25                  30

Asn Met Asp Trp Val Arg Gln Ala Pro Gly Lys Gly Leu Glu Trp Ile
        35                  40                  45

Gly Asn Ile Asn Pro Asn Ser Glu Ser Thr Ser Tyr Asn Gln Lys Phe
    50                  55                  60

Lys Gly Arg Ala Thr Leu Thr Val Asp Lys Ser Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Asp Gly Asn Arg Tyr Asp Ala Trp Phe Ala Tyr Trp Gly Gln
            100                 105                 110

Gly Thr Leu Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: 3B10 Humanised VH3 Peptide

<400> SEQUENCE: 33

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Gly Leu Glu Trp Ile
        35                  40                  45

Gly Asn Ile Asn Pro Asn Ser Glu Ser Thr Ser Tyr Asn Gln Lys Phe
    50                  55                  60

Lys Gly Arg Ala Thr Ile Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Asp Gly Asn Arg Tyr Asp Ala Trp Phe Ala Tyr Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: 3B10 Humanised VH 4 Peptide

<400> SEQUENCE: 34

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30
```

-continued

Asn Met Asp Trp Val Arg Gln Ala Pro Gly Lys Gly Leu Glu Trp Ile
        35                  40                  45

Gly Asn Ile Asn Pro Asn Ser Glu Ser Thr Ser Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
            85                  90                  95

Thr Arg Asp Gly Asn Arg Tyr Asp Ala Trp Phe Ala Tyr Trp Gly Gln
                100                 105                 110

Gly Thr Leu Val Thr Val Ser Ser
            115                 120

<210> SEQ ID NO 35
<211> LENGTH: 120
<212> TYPE: PRT
<213> ORGANISM: Artificial Sequence
<220> FEATURE:
<223> OTHER INFORMATION: 3B10 Humanised VH5 Peptide

<400> SEQUENCE: 35

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Ile
        35                  40                  45

Gly Asn Ile Asn Pro Asn Ser Glu Ser Thr Ser Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
            85                  90                  95

Thr Arg Asp Gly Asn Arg Tyr Asp Ala Trp Phe Ala Tyr Trp Gly Gln
                100                 105                 110

Gly Thr Leu Val Thr Val Ser Ser
            115                 120

<210> SEQ ID NO 36
<211> LENGTH: 106
<212> TYPE: PRT
<213> ORGANISM: Artificial Sequence
<220> FEATURE:
<223> OTHER INFORMATION: 3B10 Humanised VK 1 Peptide

<400> SEQUENCE: 36

Gln Ile Val Leu Thr Gln Ser Pro Ala Ile Leu Ser Leu Ser Pro Gly
1               5                   10                  15

Glu Arg Ala Thr Met Ser Cys Ser Ala Ser Ser Val Thr Tyr Met
            20                  25                  30

His Trp Phe Gln Gln Lys Pro Gly Lys Ala Pro Lys Leu Trp Ile Tyr
        35                  40                  45

Ser Thr Ser Ile Leu Ala Ser Gly Val Pro Ala Arg Phe Ser Gly Ser
 50                  55                  60

Gly Ser Gly Thr Ser Tyr Thr Leu Thr Ile Ser Arg Leu Glu Ala Glu
 65                  70                  75                  80

Asp Phe Ala Thr Tyr Tyr Cys Gln Gln Arg Thr Ser Tyr Pro Leu Thr

```
                    85                  90                  95

Phe Gly Gln Gly Thr Lys Leu Glu Ile Lys
            100                 105

<210> SEQ ID NO 37
<211> LENGTH: 106
<212> TYPE: PRT
<213> ORGANISM: Artificial Sequence
<220> FEATURE:
<223> OTHER INFORMATION: 3B10 Humanised VK2 Peptide

<400> SEQUENCE: 37

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Met
            20                  25                  30

His Trp Phe Gln Gln Lys Pro Gly Lys Ala Pro Lys Leu Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Ser Tyr Thr Leu Thr Ile Ser Arg Leu Glu Ala Glu
65                  70                  75                  80

Asp Phe Ala Thr Tyr Tyr Cys Gln Gln Arg Thr Ser Tyr Pro Leu Thr
                85                  90                  95

Phe Gly Gln Gly Thr Lys Leu Glu Ile Lys
            100                 105

<210> SEQ ID NO 38
<211> LENGTH: 106
<212> TYPE: PRT
<213> ORGANISM: Artificial Sequence
<220> FEATURE:
<223> OTHER INFORMATION: 3B10 Humanised VK3 Peptide

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Met
            20                  25                  30

His Trp Phe Gln Gln Lys Pro Gly Lys Ala Pro Lys Leu Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Asp Tyr Thr Leu Thr Ile Ser Arg Leu Glu Ala Glu
65                  70                  75                  80

Asp Phe Ala Thr Tyr Tyr Cys Gln Gln Arg Thr Ser Tyr Pro Leu Thr
                85                  90                  95

Phe Gly Gln Gly Thr Lys Leu Glu Ile Lys
            100                 105

<210> SEQ ID NO 39
<211> LENGTH: 106
<212> TYPE: PRT
<213> ORGANISM: Artificial Sequence
<220> FEATURE:
<223> OTHER INFORMATION: 3B10 Humanised VK 4 Peptide

<400> SEQUENCE: 39

Glu Ile Val Leu Thr Gln Ser Pro Ala Thr Leu Ser Leu Ser Pro Gly
1               5                   10                  15
```

Glu Arg Ala Thr Leu Ser Cys Ser Ala Ser Ser Val Thr Tyr Met
            20                  25                  30

His Trp Phe Gln Gln Lys Pro Gly Lys Ala Pro Lys Leu Trp Ile Tyr
        35                  40                  45

Ser Thr Ser Ile Leu Ala Ser Gly Val Pro Ala Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Thr Tyr Tyr Cys Gln Gln Arg Thr Ser Tyr Pro Leu Thr
                85                  90                  95

Phe Gly Gln Gly Thr Lys Leu Glu Ile Lys
            100                 105

<210> SEQ ID NO 40
<211> LENGTH: 106
<212> TYPE: PRT
<213> ORGANISM: Artificial Sequence
<220> FEATURE:
<223> OTHER INFORMATION: 3B10 Humanised VK 5 Peptide

<400> SEQUENCE: 40

Glu Ile Val Leu Thr Gln Ser Pro Ala Thr Leu Ser Leu Ser Pro Gly
1               5                   10                  15

Glu Arg Ala Thr Met Ser Cys Ser Ala Ser Ser Val Thr Tyr Met
            20                  25                  30

His Trp Phe Gln Gln Lys Pro Gly Lys Ala Pro Lys Leu Leu Ile Tyr
        35                  40                  45

Ser Thr Ser Ile Leu Ala Ser Gly Val Pro Ala Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Thr Tyr Tyr Cys Gln Gln Arg Thr Ser Tyr Pro Leu Thr
                85                  90                  95

Phe Gly Gln Gly Thr Lys Leu Glu Ile Lys
            100                 105

<210> SEQ ID NO 41
<211> LENGTH: 115
<212> TYPE: PRT
<213> ORGANISM: Artificial Sequence
<220> FEATURE:
<223> OTHER INFORMATION: 8H5 Humanised VH1 Peptide

<400> SEQUENCE: 41

Gln Val Gln Leu Val Gln Ser Gly Asp Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Ala Thr Leu Thr Val Asp Lys Ser Ser Ser Thr Ala Tyr
65                  70                  75                  80

Ile Glu Leu Ser Ser Leu Arg Ser Glu Asp Ser Ala Val Tyr Phe Cys
                85                  90                  95

Ala Arg Gly Asp Tyr Gly Ser Tyr Trp Gly Gln Gly Thr Leu Val Thr

```
Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: 8H5 Humanised VH2 Peptide

<400> SEQUENCE: 42

Gln Val Gln Leu Val Gln Ser Gly Asp Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Ala Thr Leu Thr Val Asp Lys Ser Ser Ser Thr Ala Tyr
65                  70                  75                  80

Ile Glu Leu Ser Ser Leu Arg Ser Glu Asp Thr Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 43
<211> LENGTH: 115
<212> TYPE: PRT
<213> ORGANISM: Artificial Sequence
<220> FEATURE:
<223> OTHER INFORMATION: 8H5 Humanised VH3 Peptide

<400> SEQUENCE: 43

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Ala Thr Leu Thr Val Asp Lys Ser Thr Ser Thr Ala Tyr
65                  70                  75                  80

Ile Glu Leu Ser Ser Leu Arg Ser Glu Asp Thr Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 44
<211> LENGTH: 115
<212> TYPE: PRT
<213> ORGANISM: Artificial Sequence
<220> FEATURE:
```

<223> OTHER INFORMATION: 8H5 Humanised VH4 Peptide

<400> SEQUENCE: 44

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: 8H5 Humanised VH5 Peptide

<400> SEQUENCE: 45

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 8H5 Humanised VK1 Peptide

<400> SEQUENCE: 46

Gln Ile Val Leu Thr Gln Ser Pro Ala Ile Leu Ser Leu Ser Pro Gly
1               5                   10                  15

Glu Arg Ala Thr Met Ser Cys Ser Ala Ser Ser Ser Ile Ser Tyr Met
            20                  25                  30

His Trp Phe Gln Gln Arg Pro Gly Gln Ser Pro Lys Arg Trp Ile Tyr

```
            35                  40                  45
Asp Thr Ser Lys Leu Ala Ser Gly Val Pro Ala Arg Phe Ser Gly Ser
         50                  55                  60

Gly Ser Gly Thr Ser Tyr Thr Leu Thr Ile Ser Ser Leu Glu Ala Glu
 65                  70                  75                  80

Asp Phe Ala Thr Tyr Tyr Cys His Gln Arg Thr Ser Tyr Pro Leu Thr
                 85                  90                  95

Phe Gly Gln Gly Thr Lys Leu Glu Ile Lys Arg
            100                 105

<210> SEQ ID NO 47
<211> LENGTH: 107
<212> TYPE: PRT
<213> ORGANISM: Artificial Sequence
<220> FEATURE:
<223> OTHER INFORMATION: 8H5 Humanised VK2 Peptide

<400> SEQUENCE: 47

Gln Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Ile Ser Tyr Met
                 20                  25                  30

His Trp Phe Gln Gln Arg Pro Gly Gln Ser Pro Arg Arg Trp Ile Tyr
            35                  40                  45

Asp Thr Ser Lys Leu Ala Ser Gly Val Pro Ala Arg Phe Ser Gly Ser
         50                  55                  60

Gly Ser Gly Thr Ser Tyr Thr Leu Thr Ile Ser Ser Leu Glu Ala Glu
 65                  70                  75                  80

Asp Phe Ala Thr Tyr Tyr Cys His Gln Arg Thr Ser Tyr Pro Leu Thr
                 85                  90                  95

Phe Gly Gln Gly Thr Lys Leu Glu Ile Lys Arg
            100                 105

<210> SEQ ID NO 48
<211> LENGTH: 107
<212> TYPE: PRT
<213> ORGANISM: Artificial Sequence
<220> FEATURE:
<223> OTHER INFORMATION: 8H5 Humanised VK3 Peptide

<400> SEQUENCE: 48

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Ile Ser Tyr Met
                 20                  25                  30

His Trp Phe Gln Gln Arg Pro Gly Gln Ser Pro Arg Arg Trp Ile Tyr
            35                  40                  45

Asp Thr Ser Lys Leu Ala Ser Gly Val Pro Ala Arg Phe Ser Gly Ser
         50                  55                  60

Gly Ser Gly Thr Asp Tyr Thr Leu Thr Ile Ser Ser Leu Glu Ala Glu
 65                  70                  75                  80

Asp Phe Ala Thr Tyr Tyr Cys His Gln Arg Thr Ser Tyr Pro Leu Thr
                 85                  90                  95

Phe Gly Gln Gly Thr Lys Leu Glu Ile Lys Arg
            100                 105

<210> SEQ ID NO 49
<211> LENGTH: 107
```

```
<212> TYPE: PRT
<213> ORGANISM: Artificial Sequence
<220> FEATURE:
<223> OTHER INFORMATION: 8H5 Humanised VK 4 Peptide

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
            20                  25                  30

His Trp Phe Gln Gln Arg Pro Gly Gln Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys His Gln Arg Thr Ser Tyr Pro Leu Thr
                85                  90                  95

Phe Gly Gln Gly Thr Lys Leu Glu Ile Lys Arg
            100                 105

<210> SEQ ID NO 50
<211> LENGTH: 107
<212> TYPE: PRT
<213> ORGANISM: Artificial Sequence
<220> FEATURE:
<223> OTHER INFORMATION: 8H5 Humanised VK5 Peptide

<400> SEQUENCE: 50

Glu Ile Val Leu Thr Gln Ser Pro Ala Thr Leu Ser Leu Ser Pro Gly
1               5                   10                  15

Glu Arg Ala Thr Met Ser Cys Ser Ala Ser Ser Ser Ile Ser Tyr Met
            20                  25                  30

His Trp Phe Gln Gln Arg Pro Gly Gln Ser Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys His Gln Arg Thr Ser Tyr Pro Leu Thr
                85                  90                  95

Phe Gly Gln Gly Thr Lys Leu Glu Ile Lys Arg
            100                 105
```